(12) United States Patent
Roussel et al.

(10) Patent No.: US 7,012,138 B1
(45) Date of Patent: Mar. 14, 2006

(54) CHIRAL POLYSACCHARIDE ESTERS, ONE OF THE METHODS FOR PREPARING THEM AND THEIR USES FOR OBTAINING OPTICALLY ENRICHED ACIDS OR FOR CHIRAL CHROMATOGRAPHY

(75) Inventors: Christian Roussel, Aubagne (FR); Brice Bonnet, Aix en Provence (FR); Innocenzo De Riggi, Marseilles (FR); Cristina Suteu, Illkirch (FR)

(73) Assignee: Universite de Droit d'Economie et des Sciences d'Aiz-Marseille, Aix en Provence Cedex (FR)

( * ) Notice: Subject to any disclaimer, the term of this patent is extended or adjusted under 35 U.S.C. 154(b) by 0 days.

(21) Appl. No.: 10/239,405

(22) PCT Filed: Dec. 2, 1999

(86) PCT No.: PCT/FR99/02988

§ 371 (c)(1),
(2), (4) Date: Jun. 1, 2001

(87) PCT Pub. No.: WO00/32638

PCT Pub. Date: Jun. 8, 2000

(51) Int. Cl.
*C08B 33/00* (2006.01)
*C08B 35/00* (2006.01)

(52) U.S. Cl. .......................... 536/56; 536/124
(58) Field of Classification Search ............... 536/1.11, 536/55.1, 55.3, 123.1, 56, 124
See application file for complete search history.

(56) References Cited

U.S. PATENT DOCUMENTS 5,202,433 A   4/1993  Okamoto et al. ........... 540/200
5,491,223 A * 2/1996  Okamoto ................... 536/18.7

FOREIGN PATENT DOCUMENTS

EP   0436722 A1 * 7/1991

OTHER PUBLICATIONS

Okamoto et al, Synlett, 1988, pp. 344-360.*
Abstract of FR 1 604 123 A (1971).
Abstract of FR 2 714 671 A (1995).
Abstract of JP 52 051 095 (1977).
E. Yashima & Y. Okamoto, Bull. Chem. Soc. Jpn. ; 3289-3307 (1995).
E. Yashima et al., SYNLETT, 1998, 344-360 "Polysacharide-based chiral LC columns".
Y. Okamoto & Y. Kaida, Journal of Chromatography A, 666 (1994), 401-419.
Rabjohn, organic Synthesis, Collective Vol. J. Wiley and Sons, 461-463, (1967).
B.S. Furniss et al., Wogel's Dexbetook of Pactice Organic Chemistry, 5 Ed., 1062-1063, (1993).
H. Van G. Elderen et al., Chirality, 6, 11-16, (1994).

* cited by examiner

*Primary Examiner*—James O. Wilson
*Assistant Examiner*—Ganapathy Krishnan
(74) *Attorney, Agent, or Firm*—Sturm & Fix LLP

(57) ABSTRACT

The present invention relates to chiral esters of polysaccharides, preferably of cellulose, amylose, β-cyclodextrin or amylopectin, obtained by reacting, in basic medium, polysaccharides (polyhydroxylated compounds) with racemic or enriched acid chlorides bearing a hydrogen and an aromatic group on their a carbon.

This acid precursor (I) may be α-phenylpropionic acid, ibuprofen, ketoprofen or naproxen and, more generally, any acid derivative which may lead to a reactive form of ketene type.

These novel asymmetric esters of polyhydroxylated compounds may be used as means of chiral enrichment, as medicinal systems with sustained and controlled release of enriched chiral active principles, these active principles consisting of the acyl parts of the esters grafted onto the hydroxyls (or even onto the amines) of the polyhydroxylated compounds, or alternatively as chiral stationary phases (CSPs).

The invention is also directed toward a process for preparing these esters, to a chiral enrichment process and to the enrichment means, the medicinal systems and the CSPs targeted above.

27 Claims, No Drawings

CHIRAL POLYSACCHARIDE ESTERS, ONE OF THE METHODS FOR PREPARING THEM AND THEIR USES FOR OBTAINING OPTICALLY ENRICHED ACIDS OR FOR CHIRAL CHROMATOGRAPHY

The field of the present invention is that of chiral separation and more particularly of compounds that are useful for this purpose. These compounds, which have chiral resolution properties, constitute the chiral stationary phases (CSPs) used in chromatographic techniques for separating enantiomers, for example high performance liquid chromatography. The performance qualities of CSPs in terms of recognition and selective chiral retention are at the heart of these separation techniques.

The present invention relates to novel esters of polyhydroxylated compounds, preferably of polysaccharides, which may be used as chiral stationary phases (CSPs), but also as chiral enrichment means and as medicinal systems with sustained and controlled release of enriched chiral active principles.

A subject of the invention is also the preparation of these novel chiral polysaccharide esters.

The present invention is moreover directed, per se toward:
novel chiral enrichment means,
novel medicinal systems with sustained and controlled release of active principles, and
novel chiral stationary phases;
comprising the chiral polysaccharide esters according to the invention.

For some years, optically active compounds have been a subject of active interest in many fields, including those relating to pharmaceutical products, to natural products, to agrochemical products, to ferroelectric liquid crystals, etc. This tendency goes hand in hand with the development of techniques for preparing, purifying and analyzing enantiomers.

As more especially regards the pharmaceutical field, the fact that living systems consist of chiral molecules and macromolecules, such as proteins, nucleic acids and polysaccharides, entails a variable sensitivity of these living organisms with respect to chiral medicinal products depending on whether the active principle is a pure enantiomer and/or a racemic mixture. Accordingly, chiral medicinal products comprising only one optical isomer as active principle(s) have appeared. These chiral medicinal products are often more effective in enantiomerically pure form than in racemic form. The detailed investigation of the pharmacokinetics, physiology, toxicology and metabolic activity of chiral medicinal products has thus had as a corollary the development of means of chiral separation, analysis and purification.

This superiority as regards the performance qualities of the pure enantiomer over the racemic mixture, which is the form most commonly obtained from a conventional synthesis, is observed not only in the pharmaceutical field, but also in the other fields in which optically pure isomers are used.

At least two methods for obtaining enantiomers in pure form are known, namely: asymmetric synthesis and the optical resolution of racemic mixtures, in particular by high performance liquid chromatography (HPLC). It is found that HPLC has become an essential technique for the research into and development of chiral medicinal products. Thus, there are at least 100 chiral stationary phases commercially available.

Generally, two types of CSP are distinguished: those prepared from small chiral molecules and those consisting of polymers which have an optical resolution power. CSPs based on small chiral molecules are prepared by chemical bonding of small chiral molecules to a support, conventionally silica gel. The ability for chiral recognition of these CSPs is relatively predictable, given the chirality of the small molecules themselves.

As regards polymeric CSP supports, this is a different story as regards the predictability of their ability for chiral recognition, since this recognition cannot be deduced from that of the monomer unit.

Among the chiral stationary phases CSP most commonly used are those consisting of polysaccharide esters and, more especially, of cellulose or amylose esters. These are, for example, cellulose triacetates, tribenzoates, trisphenylcarbamates or tricinnamates, or amylose trisphenylcarbamates or trisphenylethyl-carbonates. The registered trademark denoting cellulose esters is Chiralcel®, while that denoting amylose esters is Chiralpack® as regards the products sold by the company Daicel.

These polyhydroxylated compounds, namely cellulose and amylose polysaccharides, are among the optically active natural polymers that are most widely available. Their derivatization by esterification makes it possible to increase their capacity for chiral recognition.

As examples of known polysaccharide esters used in particular as CSPs in chromatography, reference will be made to those disclosed in the following articles:
E. YASHIMA & Y. OKAMOTO, *Bull. Chem. Soc. Jpn.*; 3289–3307 (1995),
E. YASHIMA et al., SYNLETT, 1998, 344–360 *"Polysaccharide-based chiral LC columns"*,
Y. OKAMOTO & Y. KAIDA, *Journal of Chromatography A*, 666 (1994), 403–419.

The cellulose or amylose esters disclosed in these articles have the characteristic that the acid or the acid derivative used to form the esters after combination with the hydroxyls does not comprise a stereogenic center. The only chiral centers are those of the polysaccharide.

The acids or derivatives thereof, which are precursors of the abovementioned esters, may be of the alkyl type, such as acetic acid and its derivatives, or of the aromatic type, such as substituted or unsubstituted benzoic acid or substituted or unsubstituted cinnamic acid.

None of these acid precursors contains an asymmetric carbon located α to the COX reactive function.

In addition to their uses in chiral separation, it should be noted that cellulose acetates are used in various forms in the packaging industry and in photography.

Patent application EP 0 316 270 discloses esters of cellulose and of aromatic acid or of aromatic and aliphatic acid, which are in the form of partially crystalline spherical particles, with a mean diameter of from 1 to 200 μm and a specific surface of between 10 and 300 m²/g. These cellulose esters are intended to be used as stationary phase in a chromatography process more especially suitable for the separation of racemates. The acids which are the precursors of the esters according to this European patent application correspond to the formula:

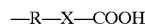

X possibly being a direct bond, a $C_1$–$C_4$ alkylene, a $C_2$–$C_4$ alkenylene, an alkylidene or an alkylnilene and R is a mono-, bi- or tricyclic residue, preferably a monocyclic residue and in particular a $C_6$–$C_{14}$ aryl or a heteroaryl.

Said European patent application does not teach novel esters or polysaccharides which may have advantageous properties as regards chiral separation and chiral enrichment.

In this state of the art, one of the essential objectives of the present invention is to provide novel esters of polyhydroxylated—and optionally polyamino—oligomers and/or polymers which have improved chiral properties.

Another essential objective of the present invention is to propose novel polyhydroxylated esters, preferably polysaccharide esters, which are particularly suitable as a means of chiral enrichment which is different from the techniques of chromatographic separation and/or as a chiral chromatography support for separating enantiomers.

Another essential objective of the present invention is to provide esters of polyhydroxylated compounds (oligomers and/or polymers) which give high-quality performance in terms of chiral separation and which may be obtained simply and economically.

Another essential objective of the invention is to provide a process for preparing esters of polyhydroxylated compounds, preferably of polysaccharides, which are effective in chiral separation and/or chiral enrichment; such a process needs to be industrial and thus inexpensive to implement.

Another essential objective of the present invention is to provide a novel means of chiral enrichment for the production of pure enantiomers.

Another essential objective of the invention is to provide a novel medicinal system for sustained and controlled release of active principles, and in particular of active principles in the form of optically pure isomers; such a process needs to be economical and simple to implement.

Another essential objective of the present invention is to provide novel chiral stationary phases or supports, that have a low cost price and high performance qualities, for chromatography and in particular for high performance liquid chromatography.

Having set themselves these objectives, among others, the inventors have, to their credit, prepared and characterized novel esters of polyhydroxylated compounds (monomers, oligomers, co-oligomers, polymers and copolymers), these multiple-OH compounds preferably being polysaccharides. These novel esters have the characteristic of being chiral and of being obtained from an acid precursor comprising at least one stereogenic center (asymmetric carbon) preferably located α to the reactive function, which is more particularly carboxylic.

It results therefrom that the present invention relates firstly to esters of polyhydroxylated—optionally polyamino—compounds, preferably of polysaccharides, characterized in that they are chiral and in that they are obtained:

by reacting at least one polyhydroxylated compound and at least one acid precursor or derivative of formula (I):

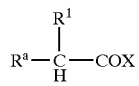

(I)

in which:
X corresponds to a hydroxyl or a halogen, preferably chlorine, $R^a$ and $R^1$ corresponding to hydrogen or to a hydrocarbon-based radical preferably chosen from alkyls, alkenyls, aryls, aralkyls, aralkenyls, alkylaryls and alkenylaryls;
→$R^a$ even more preferably representing an aryl, an aralkyl, an aralkenyl, an alkylaryl or an alkenylaryl, and
→$R^1$ even more preferably representing a linear or branched and/or cyclic $C_1$–$C_{20}$ and advantageously $C_1$–$C_6$ alkyl; and in that
they contain at least one stereogenic center introduced by the acid precursor or derivative (I), and
the acyl units attached to said polyhydroxylated compound, preferably the polysaccharide, not being all of identical chirality.

The acids resulting from the hydrolysis of said esters are in fact not all of the same chirality, as may be observed by hydrolyzing the esters using a base, preferably a hydroxylated base such as lithium hydroxide.

The esters concerned according to the invention are those resulting from reactions between COX and OH functions.

It should be noted that, when the polyhydroxylated compounds also comprise reactive functions of amine type, the acid precursors or derivatives (I) may react with these amine functions (—COX+—NHR) to form amide bonds.

It results therefrom that, throughout the present specification, the term "chiral esters" will denote both chiral esters in the strict sense and chiral esters comprising, in addition, acyl portions of the compounds (I) attached to the polyhydroxylated compound(s) via amide bonds.

For the purposes of the invention, the polyhydroxylated compounds are chiral products (for example polymers) comprising at least two hydroxyl units and optionally at least two amine units. This term "polyhydroxylated compound" thus encompasses both compounds comprising only OHs and compounds comprising OHs and amine functions.

In one embodiment of the invention, said acyl units attached to said polyhydroxylated compound are mainly of R configuration.

More particularly, the proportion of said acyl units of R configuration is between 50% and 70%.

In another embodiment, said acyl units attached to said polyhydroxylated compound are mainly of S configuration.

More particularly, the proportion of said acyl units of S configuration is between 50% and 60%.

The formula of the ester of polyhydroxylated compound according to the present invention is thus obtained by replacing a hydrogen atom of at least one hydroxyl or amine group of said polyhydroxylated compound with a residue

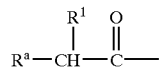

the stereogenic center of which may be of different chirality from that of the starting acid chloride reagent of formula (1).

The esters according to the invention are obtained by passage from the acid precursor or derivative (I) in one (or more) intermediate reactive form(s) in equilibrium with the prochiral species of ketene type containing at least one stereogenic center introduced via the acyl portion of the acid precursor or derivative (I), the chirality of which does not depend on the chirality of the starting acid precursor. The chiral acyl units are attached in a specific organization which depends on the sensitivity of the various sites of attachment of the polyhydroxylated compound with regard to the prochiral intermediate reactive species of ketene type derived from the acid precursor (I). In other words, the chirality of each acyl unit attached to the primary and secondary alcohols of the polyhydroxylated compound, preferably of the polysaccharide, does not depend on the initial configuration of the starting acid precursor or derivative (I), but is essentially controlled by the polyhydroxylated compound and by the nature of the base(s) used, and also depends on the nature of the intermediate reactive species derived from the acid precursor or derivative (I), in equilibrium with prochiral species of ketene type.

These novel esters have the following advantages:

They open up advantageous perspectives as regards applications of chiral enrichment type, of medicinal systems for the sustained and controlled release of active principle when this active principle constitutes the acid precursor or derivative (I) of which the acyl unit is composed or as a chiral chromatography stationary phase for resolving racemates.

The esters thus formed have a relaxed three-dimensional structure, that is to say a structure whose stress energies are minimized, in particular from the point of view of interactions between the various stereogenic centers present on the polyhydroxylated polymer and the acyl units of esters, or even of amides, introduced.

This relaxation makes it possible to improve the properties of these esters in terms of application of chiral enrichment type, of medicinal systems for the sustained and controlled release of active principle, when this active principle constitutes the acid precursor or derivative (I) of which the acyl units are composed, or as a chiral chromatography stationary phase for resolving racemates.

It is not necessary to use an enantiomerically pure, expensive acid precursor or derivative. The reason for this is that a racemic mixture or scalemic mixture (i.e. a mixture of the two enantiomers in any proportions), which is less expensive, is entirely sufficient.

As regards the acid precursor or derivative (I), the ones which are preferred in accordance with the invention are those of formula (I) in which:

$R^a$ corresponds to a substituent comprising at least one phenyl and/or at least one naphthyl, and $R^1$ corresponds to a methyl, an ethyl or a propyl.

The acid precursors or derivatives (I) that are most reactive are acid halides, acid chlorides being particularly suitable. Thus, X preferably corresponds to Cl in formula (I) of the acid precursor or derivative.

As examples of acid precursors or derivatives (I), preferably of acid chlorides, reference may be made to examples of novel acids leading to the precursors (I). These novel acids correspond, for example, to the general formula (II):

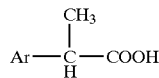

in which Ar represents an aromatic radical.

The following compounds corresponding to this formula (II) may be considered: α-phenylpropionic acid, α-(p-chlorophenyl)propionic acid, 2-[3-benzoylphenyl]-propionic acid (ketoprofen), α-(3,5-dimethylphenyl)-propionic acid, α-(2-thiophenyl)propionic acid, α-(p-methylphenyl)propionic acid, α-methyl-4-[isobutyl]-phenylacetic acid (ibuprofen), 6-methoxy-α-methyl-2-naphthaleneacetic acid (naproxen), a nonsteroidal anti-inflammatory acid.

Ibuprofen, ketoprofen and naproxen are well-known nonsteroidal anti-inflammatories. They are chiral medicinal products of carboxylic nature, among a series of others which may form esters with polyhydroxylated compounds in accordance with the invention. These chiral active principles (II) illustrate the possibilities of application of the invention in the chiral pharmaceutical industry (purification of enantiomers, chiral enrichment, separation of pure optical isomers).

These medicinal or nonmedicinal novel acids (II) from which the precursors (I) may be obtained are commercially available, but may be prepared via synthetic routes that are well known to those skilled in the art. For example, mention will be made of a conventional synthetic route which involves three successive steps:

carboxyethylation of an arylacetonitrile [RABJOHN, *Organic Synthesis*, Collective Vol. J. WILEY and Sons, 461–463, (1967)]:

methylation immediately followed by a carboxylation [M. BERCOT-VATTERONI et al., *Bull. Soc. Chim. Fr.*, 1820–1821, (1961)], hydrolysis of nitrile [B. S. FURNISS et al., *Wogel's Dexbetook of Practice Organic Chemistry*, 5 Ed., 1062–1063, (1993)].

Without wishing to be bound by theory, it may be pointed out that one of the important reaction intermediates for obtaining the esters according to the invention is a reactive form derived from compounds (II) and (I). In this instance, it is a ketene $ArR_1C=C=O$. This prochiral intermediate reactive form of ketene type is transient.

The ketene is preferably obtained via an acid halide intermediate (e.g. a chloride), but it is not excluded to form this ketene by acting on the starting carboxylic acid (original acid II), for example, in a nonlimiting manner, using reagents such as dicyclohexylcarbodiimide, TsCl or 1-methyl-2-chloropyridinium iodide (Mukaiyama reagent).

The reactive functions capable of reacting with the acid precursors or derivatives (I) (preferably acid chlorides) are hydroxyl functions borne by compounds which may be monomers and/or (co)oligomers and/or (co)polymers. Mono-, oligo- and polysaccharides are the polyhydroxylated compounds that are preferred in accordance with the invention. These mono- and/or oligo- and/or polysaccharides are hydrogenated or unhydrogenated.

In practice, the polyhydroxylated compounds are polysaccharides selected from celluloses and/or derivatives thereof and/or starches and derivatives thereof. The monomer units of which these polysaccharides are composed and which are more especially selected are "glucose" units linked via $\beta_{1-4}$ bonds in the case of cellulose and $\alpha_{1-4}$ bonds in the case of amylose and optionally $\alpha_{1-6}$ bonds in the case of amylopectin, as regards starch.

As other examples of polysaccharides which may be suitable for forming the esters according to the invention, mention may be made of xylans, mannans, pullulans, curdlans, chitosans, dextrans, inulins, etc.

As already mentioned above, hydroxyls are not the only reactive functions with which the acid precursors or derivatives are capable of reacting. Thus, amine functions present on the polyhydroxylated compounds may be the basis of the grafting of chiral units derived from (I) by formation of amide bonds.

This is thus the case in polymers of the chitosan type.

The fact that polysaccharides are preferred does not, however, exclude esters formed from oligosaccharide of cello-oligosaccharide or malto-oligosaccharide type. They may also be cyclic oligosaccharides, such as α-, β- and γ-cyclodextrins.

When the polyhydroxylated compound is a polysaccharide consisting of $C_6$ monosaccharide monomer units, the esters of the invention are characterized in that the chirality resulting from each ester formed is different for each of the three alcohol functions of each monomer, namely: the primary alcohol function of the $C_6$ and the two secondary alcohol functions, of $C_2$ and $C_3$ respectively.

The esters according to the invention may also be defined by the degree of substitution (DS) of the alcohol functions of the monomer units which constitute the polyhydroxylated compound. Thus, for the purposes of the invention, the degree of substitution DS corresponds to the number of equivalents of acyl units introduced onto the support (that is to say the polymer) per monomer unit.

Mention is made in particular of esters in which the degree of substitution DS of each monomer unit of said polyhydroxylated compound is between 0.5 and 3.

Thus, in the case of polysaccharides, it is possible to have esters whose DS is in the region of 1 and in which the alcohol function which has reacted is mainly the primary alcohol function. For esters with a DS in the region of 2, it is mainly the primary alcohol function and secondary alcohol function in position 2 of the 5-carbon or 6-carbon monosaccharide unit which react with the acid precursor or derivative (I). Finally, in esters with a DS in the region of 3, all the alcohol functions of the saccharide monomer are involved in the esterification.

The DS values, evaluated by solid phase Fourier transform infrared spectroscopy, are measured by microanalysis of the elements and by proton magnetic resonance (200 MHz) when the solubility of the esters obtained is sufficient.

As results from the definition of the esters according to the invention given above, and also from the formula of the acid precursors or derivatives (I) included in this definition, the nature of the acyl units of said esters may be different from one esterified alcohol function to another on the polyhydroxylated compound. Such esters are referred to as "mixed esters" according to the nomenclature used in the present specification. Mixed esters are those comprising at least one acyl unit derived from an asymmetric acid precursor or derivative (I), the other acyl units possibly being derived from asymmetric or non-asymmetric and different acid precursors or derivatives (I). This latter embodiment of the invention corresponds to the case in which the esters are characterized in that they are obtained by reacting at least one other acid precursor or derivative (I') which is different from the acid precursor(s) or from the derivative(s) (I), with the polyhydroxylated compound(s);

this other reagent (I') being chosen from the chiral compounds used in the present invention or from chiral or achiral compounds in the following nonlimiting list: acetic acid, propionic acid, benzoic acid, carbamic acid and derivatives.

Advantageously, mixed esters comprising various asymmetric or non-asymmetric acid substituents may be obtained by sequentially introducing the various acid precursors or derivatives (I), preferably the various acid chlorides.

The degrees of substitution DS of these mixed esters may be controlled by the introduction sequences and by other methodological arrangements specific to the esterification process. The sequential additions of the various precursors may be carried out in the same reactor or, and it is preferred to work in this way, by purification and characterization between each addition.

Among the esters according to the invention, mention is made more particularly of the following esters mainly comprising said acyl units of R configuration, preferably comprising between 50% and 70% of units of R configuration:

cellulose α-phenylpropionate
amylose α-chlorophenylpropionate
cellulose α-chlorophenylpropionate
amylose α-chlorophenylpropionate (you have mentioned this twice)
cellulose α-(3,5-dimethylphenyl)propionate
cellulose α-(para-methylphenyl)propionate
cellulose α-(2-thiophenyl)propionate
a mixed cellulose ester of α-phenylpropionic acid and of ketoprofen
cellulose ketoprofenate
amylose ketoprofenate
cellulose ibuprofenate
cellulose naproxenate
amylose naproxenate
beta-cyclodextrin naproxenate
an ester of cellulose or of amylose and of nonsteroidal anti-inflammatory acid.

Mention is also made of esters mainly comprising said acyl units of S configuration, preferably comprising between 50% and 60% of units of S configuration:

cellulose α-phenylpropionate
amylose α-chlorophenylpropionate
cellulose α-chlorophenylpropionate
amylose α-chlorophenylpropionate (you have mentioned this twice)
cellulose α-(3,5-dimethylphenyl)propionate
cellulose α-(para-methylphenyl)propionate
cellulose α-(2-thiophenyl)propionate
a mixed cellulose ester of α-phenylpropionic acid and of ketoprofen
cellulose ketoprofenate
amylose ketoprofenate
cellulose ibuprofenate
cellulose naproxenate
amylose naproxenate
beta-cyclodextrin naproxenate
an ester of cellulose or of amylose and of nonsteroidal anti-inflammatory acid.

According to another of its aspects, the present invention relates to a process for preparing esters of polyhydroxylated compounds, preferably of polysaccharides, in particular of the type described above. This process is characterized in that it consists essentially in reacting at least one polyhydroxylated compound with at least one acid or derivative of formula (I), preferably in basic medium.

According to one preferred arrangement of the invention, at least one acid chloride is used as reagent (I) and the esters formed are recovered by carrying out at least one precipitation/dissolution sequence.

In practice, these esters are obtained according to the invention by reaction, for example, of an acid chloride (obtained by well-known reactions starting with the corresponding carboxylic acid, cf. above) with a polyhydroxylated compound, preferably a predried polysaccharide, in the presence of a base, advantageously a tertiary nitrogen base (for example pyridine), alone or as a mixture with another base or a cosolvent (e.g. pyridine, pyridine/triethylamine, pyridine/toluene, etc.).

The preparation of the acid chlorides is disclosed, for example, in: H. Van. G. ELDEREN et al., *Chirality*, 6, 11–16, (1994).

The esterification reaction may optionally be catalyzed using a suitable catalyst, depending on the nature of the precursor of acid chloride type involved and depending on the desired degree of substitution. The catalyst may be, for example, 4-dimethylaminopyridine (DMAP).

The reaction medium is stirred at a temperature of between 25° C. and 120° C. for a period of between 1 h and 48 h. The esters according to the invention are recovered by precipitation from an alcohol such as methanol, and then purified by a repeated sequence of precipitations from alcohol (methanol) and dissolution in an organic solvent, such as dichloromethane.

This preferred mode for preparing the esters according to the invention, in accordance with a process which is also of the invention, obviously applies to the mixed esters defined above, by including the step of sequential addition of the acid precursor or derivative (I) (acid chloride).

This corresponds to a variant of the process of the invention in which at least one other acid or derivative (I') which is different from the acid(s) or from the derivative(s) (I) is used in the esterification, this additional reagent preferably being chosen from the compounds used in the present invention or in the following nonexhaustive list: acetic acid, propionic acid, benzoic acid, carbamic acid, and derivatives, etc.

According to another variant, the esters according to the invention may be obtained without proceeding via the acid halides (preferably chlorides) of formula (I), but by directly reacting one or more suitable reagents with the acid precursor (I) in carboxylic acid form.

As examples of such reagents, mention may be made of dicyclohexylcarbodiimide, TsCl or 1-methyl-2-chloropyridinium iodide (Mukaiyama reagent).

These two reaction routes both lead to a reaction intermediate of ketene type:

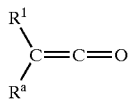

$R_1$ and $R^a$ being as defined in formula (I).

The present invention also relates to the chiral enrichment of racemates. This application of chiral esters, preferably polysaccharide esters, follows from their advantageous characteristic according to which the chirality resulting from each acyl unit attached to the primary and secondary alcohols of the polysaccharide does not depend on the initial configuration of the original acid (II), but is essentially controlled by the polyhydroxylated compound and by the nature of the base(s) used, and also depends on the prochiral nature of the intermediate reactive species of ketene type used. As an illustrative example, the chromatographic analysis of the acids derived from the hydrolysis of the phases synthesized from naxopren S (+) and from racemic naxopren shows similar enrichments.

The chirality resulting from each ester formed has the particular feature that it is different for each of the three alcohol functions of the saccharide monolymer, when the polymer considered is a polysaccharide consisting of $C_6$ saccharide monomers. This means that, as an illustrative and nonlimiting example, and in an entirely surprising and unexpected manner, the hydrolyses of esters, such as cellulose naproxenate formed in pyridine (with or without catalytic DMAP), reveal that the acid residues obtained after hydrolysis are mainly of R configuration for the esters whose acyl units are attached to the primary alcohol and secondary alcohol in positions 6 and 2, respectively, of the glucose unit, whereas the acid residues attached, before hydrolysis, to the secondary alcohol in position 3 of the glucose unit are very predominantly of S configuration. When the esters are mono-, di- or trisubstituted cellulose α-phenylpropionates, it is noted that the primary alcohol orients toward an R configuration of the attached acyl unit and that a compensation of the residues derived from the hydrolysis of the esters specific to the two secondary alcohol functions operates, to give, in fine, a final ratio in favor of the R configuration.

Thus, by modifying:
  the differences in affinity of each of the reactive forms derived from the acid precursor or derivative (I) with respect to the various hydroxyl sites (primary or secondary) of the polyhydroxylated compound (preferably of the polysaccharide)
  the nature of the base(s) used, and
  the differences in sensitivity of the various esterified sites with respect to hydrolysis, it is possible to isolate one or other of the two enantiomers in an optically pure manner, or to obtain a mixture of enantiomers which is enriched in one of the two forms.

As a result thereof, a subject of the present invention is also a process of chiral enrichment of racemates, characterized in that it consists essentially:

☐1☐—in using acids or derivatives in racemic or enantiomerically pure form, as starting materials to prepare the esters as defined above or the esters as obtained by the process also presented above, and ☐1☐—in hydrolyzing the esters thus formed, preferably using a base and even more preferably using a hydroxylated base, in particular lithium hydroxide.

This process according to the invention thus makes it possible, in an entirely advantageous manner, to achieve, for example, an overall enrichment of 36%, corresponding to a 68/32 ratio, after esterification of cellulose, in pyridine and at room temperature, using racemic α-phenylpropionic acid chloride, followed by hydrolysis of the cellulose α-phenylpropionate ester formed using a strong base, preferably chosen from alkali metal hydroxides such as, for example, lithium hydroxide.

In practice, the hydrolyses are in fact performed using lithium hydroxide monohydrate, in a non-racemizing manner. The enantiomeric composition of the acid recovered after hydrolysis is measured by chiral HPLC on stationary phases, such as those sold by the company Daicel.

The enrichment is possible due to the differences in affinity of each of the reactive forms derived from the acid precursor or derivative (I) with respect to each type (primary or secondary) of hydroxylated sites, due to the nature of the base(s) used and due to the differences in sensitivity with respect to the hydrolysis of these various esterified sites.

According to one variant of the enrichment process according to the invention, before the hydrolysis -2- stricto sensu, a step -1a- of deracemization of the chiral esters of the invention is included, preferably using a nitrogen base.

Such a deracemization, the effect of which is to improve the relaxation of the polymer, is particularly advantageous in the aim of preferentially generating a given configuration of the stereogenic center introduced, so as to be able to recover, after hydrolysis, mixtures of optically enriched acids.

According to this variant, the enrichment process comprises the following essential steps:
- -1- use of acids or derivatives in racemic or enantiomerically pure form, as starting materials, to prepare the esters as defined above or the esters as obtained by the process also presented above;
- -1a- deracemization, preferably using one or more nitrogen bases included in the following nonlimiting list: triethylamine, pyridine, picolines, DMAP, DABCO, quinoline;
  this deracemization allowing, firstly, relaxation of the esterified polyhydroxylated compound and, secondly, each ester function to adopt the absolute configuration which is energetically most stable;
- -2- total or partial hydrolysis of the ester units, preferably using a strong base, even more preferably using a strong base selected from alkali metal hydroxides (LiOH being most especially selected), so as to predominantly release one of the two enantiomers of the starting acid precursor or derivative (II).

In addition to this chiral enrichment process, the present invention is also directed toward, per se, a means of chiral enrichment for carrying out above said process, this means being characterized in that it comprises the esters as defined above and/or the esters obtained by the process.

To complete the register of the applications of the chiral esters of polysaccharides according to the invention, it will be recalled that they may be used as chiral chromatography support for the separation of enantiomers. As a result, the present invention relates to an enantioselective chiral chromatography support, characterized in that it comprises the esters as defined above and/or the esters obtained by the process also described above.

The examples which follow reveal the advantageous results obtained using the esters according to the invention, in the context of their chromatographic evaluation as chiral stationary phase.

It especially emerges from these examples that the chiral stationary phases according to the invention may have orders of elution that are the inverse of those of commercial chiral stationary phases.

Since the esters according to the invention may consist, as regards their original acids (II) giving rise to the precursors, of chiral medicinal active principles, and given, moreover, the enrichment process according to the invention which makes it possible by hydrolysis of the esters to obtain optically pure acids, it appears to be entirely judicious to prepare medicinal systems with sustained and controlled release of active principles, comprising the esters according to the invention.

Thus, the present invention is also directed toward a medicinal product, characterized:
- in that it comprises esters as defined above and/or esters obtained by the process which is also defined above, the acid precursor(s) of the esters constituting the active principle(s), and
- in that it is capable of releasing the active principle(s) in a sustained and controlled manner, by hydrolysis.

Specifically, the hydrolysis according to various kinetics of the esters of the invention makes it possible to deliver, in a controlled and sustained manner in vivo and in vitro, chiral acid active principles (for example of nonsteroidal anti-inflammatory type) having a preferential chiral configuration. Now, it is known that chiral medicinal products are all the more active when they are in optically purified form, hence the unquestionable advantage of the medicinal product according to the invention. This product also has the advantage of being particularly well tolerated, since it is known that polyhydroxylated compounds (preferably polysaccharides) which constitute an inert support for chiral active principles are biocompatible, biodegradable and nontoxic.

The present invention will be understood more clearly in the light of the examples which follow, from which also emerge all of its advantages and implementation variants in terms of products, processes and applications.

EXAMPLES

These examples comprise, in section A, the synthesis of the acid chlorides or, in other words, of the acid precursors or derivatives (I).

Section B is devoted to the synthesis of the esters (Examples 1 to 34).

Section C is devoted to the process of enrichment according to the invention by hydrolysis of the esters of Examples 1 to 34, Examples 41, 43 and 63 to 67 relating more particularly to the variant comprising the step of deracemization of the enrichment process (Examples 35 to 62).

Section D relates to the chromatographic evaluation of the esters synthesized and used as chiral stationary phase. This chromatographic evaluation of cellulose esters in accordance with the invention is carried out by the "microbatch" method, in a 99/1 hexane/2-propanol eluent, carried out on 4 racemates (benzoin, Tröger's base, trans-stilbene oxide, Pirkle's alcohol) of Professor Okamoto's series.

Preamble

The general reaction scheme is as follows:

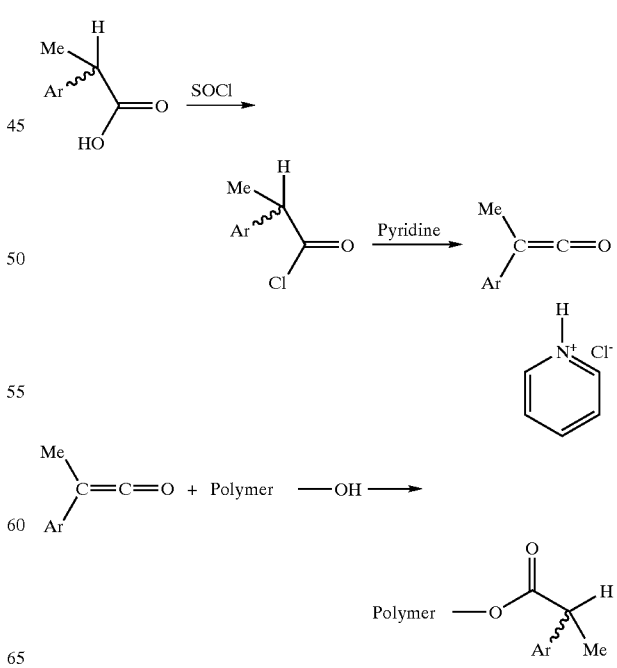

A—Syntheses of Acid Chlorides: Precursors-ACIDs or ACID Derivatives (I)

Synthesis of α-Phenylpropionic Acid Chloride:

3.50 g (M=150 g; 24 mmol) of α-phenylpropionic acid and 100 ml of $CH_2Cl_2$ are placed in a 250 ml two-necked round-bottomed flask fitted with a condenser on which is mounted a calcium chloride guard tube, and an addition funnel. The mixture is stirred at room temperature. 17.5 ml (10 eq) of freshly distilled thionyl chloride (M=119 g) are then added dropwise. After addition, the mixture is maintained at the reflux point of the $CH_2Cl_2$ for 2 h. After evaporation of the reaction mixture under reduced pressure, 3.91 g (M=168.5 g; 23.3 mmol) of α-phenylpropionic acid chloride are obtained in the form of a pale yellow solid, i.e. a yield of 96%.

$^1$H NMR ($CDCl_3$, 200 MHz) δ (ppm): 1.48 (d, 3H, J=7.0 Hz, α-$CH_3$); 4.00 (q, 1H, J=7.0 Hz, α-CH); 7.13–7.30 (m, 5 aromatic H).

Synthesis of α-(p-Chlorophenyl)Propionic Acid Chloride:

The procedure is identical to that for the synthesis of α-phenylpropionic acid chloride. Starting with 4.54 g (M=184.5 g, 24.6 mmol) of α-(p-chlorophenyl)propionic acid and 17.9 ml (10 eq) of thionyl chloride, 5.00 g (M=203 g, 24.6 mmol) of α-(p-chlorophenyl)propionic acid chloride are obtained, i.e. a yield of 100%.

$^1$H NMR ($CDCl_3$, 200 MHz) δ (ppm): 1.58 (d, 3H, J=7.0 Hz, α-$CH_3$); 4.10 (q, 1H, J=7.0 Hz, α-CH); 7.21 (dd, 2 aromatic H), J=8.8 Hz and J=2.2 Hz); 7.36 (dd, 2 aromatic H, J=8.6 Hz and J=2.0 Hz).

Synthesis of Ketoprofen (2-[3-Benzoylphenyl]Propionic Acid) Chloride:

The procedure is identical to that for the synthesis of α-phenylpropionic acid chloride. Starting with 4.69 g (M=254.3 g, 18.4 mmol) of ketoprofen and 13.4 ml (10 eq) of thionyl chloride, 5.26 g (M=272.8 g, 18.2 mmol) of ketoprofen chloride are obtained, i.e. a yield of 99%.

$^1$H NMR ($CDCl_3$, 200 MHz) δ (ppm): 1.62 (d, 3H, J=7.0 Hz, α-$CH_3$); 4.20 (q, 1H, J=7.0 Hz, α-CH); 7.43–7.64 (m, 5 aromatic H); 7.71–7.83 (m, 4 aromatic H).

Synthesis of α-(3,5-Dimethylphenyl)Propionic Acid Chloride:

The procedure is identical to that for the synthesis of α-phenylpropionic acid chloride. Starting with 2.32 g (M=178 g, 13 mmol) of α-(3,5-dimethylphenyl)propionic acid and 9.5 ml (10 eq) of thionyl chloride, 2.53 g (M=196.5 g, 12.9 mmol) of α-(3,5-dimethylphenyl)propionic acid chloride are obtained, i.e. a yield of 99%.

$^1$H NMR ($CDCl_3$, 200 MHz) δ (ppm).

Synthesis of α-(p-Methylphenyl)Propionic Acid Chloride:

The procedure is identical to that for the synthesis of α-phenylpropionic acid chloride. Starting with 1.725 g (M=164 g, 10.5 mmol) of α-(p-methylphenyl)propionic acid and 7.7 ml (10 eq) of thionyl chloride, 1.92 g (M=182.5 g, 10.5 mmol) of α-(p-methylphenyl)propionic acid chloride are obtained, i.e. a yield of 100%.

$^1$H NMR ($CDCl_3$, 200 MHz) δ (ppm): 1.49 (d, 3H, J=7.0 Hz, α-$CH_3$); 2.26 (s, 3H, p-$CH_3$); 4.00 (q, 1H, J=7.0 Hz, α-CH); 7.10 (s, 4 aromatic H).

Synthesis of α-(2-Thiophenyl)Propionic Acid Chloride:

The procedure is identical to that for the synthesis of α-phenylpropionic acid chloride. Starting with 1.515 g (M=156 g, 9.7 mmol) of α-thienylpropionic acid and 7.1 ml (10 eq) of thionyl chloride, 1.6 g (M=174.5 g, 9.2 mmol) of α-thienylpropionic acid chloride are obtained, i.e. a yield of 95%.

$^1$H NMR ($CDCl_3$, 200 MHz) δ (ppm): 1.68 (d, 3H, J=7.2 Hz, α-$CH_3$); 4.38 (q, 1H, J=7.2 Hz, α-CH); 7.26–7.30 (m, 2 aromatic H); 7.52 (dd, 1 aromatic H, J=4.9 Hz and J=1.5 Hz).

Synthesis of Ibuprofen (α-Methyl-4-[2-Methylpropyl]-Phenylacetic Acid) Chloride:

The procedure is identical to that for the synthesis of α-phenylpropionic acid chloride. Starting with 5 g (M=206 g, 24 mmol) of ibuprofen (α-methyl-4-[2-methylpropyl] phenyl acetic acid) and 17.5 ml (10 eq) of thionyl chloride, 5.2 g (M=224.5 g, 23.2 mmol) of ibuprofen chloride are obtained, i.e. a yield of 97%.

$^1$H NMR ($CDCl_3$, 200 MHz) δ (ppm): 0.90 (d, 6H, J=6.6 Hz, 2×$CH_3$); 1.57 (d, 3H, J=7.0 Hz, α-$CH_3$); 1.85 (mhept, 1H, J=6.6 Hz, 1 isopropyl H); 2.47 (d, 2H, J=7.2 Hz, —$CH_2$Ar); 4.09 (q, 1H, J=7.0 Hz, —CHAr); 7.12–7.20 (m, 4 aromatic H).

Synthesis of Naproxen (6-Methoxy-α-Methyl-2-Naphthaleneacetic Acid) Chloride:

The procedure is identical to that for the synthesis of α-phenylpropionic acid chloride. Starting with 8.50 g (M=230 g; 37 mmol) of S-naproxen ((+)-6-methoxy-α-methyl-2-naphthalene acetic acid) and 27 ml (10 eq) of thionyl chloride, 9.18 g (M=248.5 g) of naproxen chloride are obtained, i.e. a yield of 100%.

$^1$H NMR ($CDCl_3$, 200 MHz) δ (ppm): 1.67 (d, 3H, J=7.0 Hz, α-$CH_3$); 3.92 (s, 3H O—$CH_3$); 4.25 (q, 1H, J=7.0 Hz, α-CH); 7.13 (d, 1 aromatic H, J=2.5 Hz); 7.17 (dd, 1 aromatic H, J=8.8 Hz and J=2.5 Hz); 7.35 (dd, 1 aromatic H, J=8.5 Hz and J=1.9 Hz); 7.68 (d, 1 aromatic H, J=1.5 Hz); 7.73 (d, 1 aromatic H, J=8.8 Hz); 7.75 (d, 1 aromatic H, J=8.5 Hz).

B—Synthesis of the Esters

Example 1

Synthesis of Cellulose α-Phenylpropionate in Pyridine (Reaction for 48H)

0.4 g (2.5 mmol) of Avicel microcrystalline cellulose (Merck 2331, M=[(162)n]g based on the glucose monomer), predried overnight at 120° C. in a vacuum oven, and 40 ml of pyridine, predistilled and placed over KOH, are placed in a 100 ml three-necked round-bottomed flask fitted with a condenser on which is mounted a calcium chloride guard tube, an addition funnel and a thermometer. The mixture is stirred and heated at 80° C. for one hour. The mixture is cooled to room temperature and 3.5 g (21 mmol, 8.5 equivalents) of freshly prepared racemic α-phenylpropionic acid chloride are added dropwise. The reaction is maintained at 115° C. for 48 h.

After cooling, the reaction mixture is poured into 100 ml of methanol with stirring. The precipitate formed is recovered by filtration and then dissolved in 30 ml of dichloromethane. The solution is filtered and concentrated under reduced pressure. The residue is poured into 100 ml of methanol with stirring and the grafted polymer is recovered, by filtration, in the form of a dark-colored powder. These dissolution-precipitation operations are carried out a second time. The product obtained is dried in a vacuum oven for two hours at 50° C. 1.23 g (yield=89% based on a trisubstitution)

of a cellulose α-phenylpropionate chiral polymer with a degree of substitution (DS) of 2.94 determined by elemental analysis are obtained.

Analyses:

IR(KBr) $v_{max}$ (cm$^{-1}$): 3100–2800 (—CH$_3$), 1760 (C=O), 1610/1510/710 (para aromatic C=C), 1480 (δas-CH$_3$), 1170 and 1090 (C=O/C—O).

$^1$H NMR (CDCl$_3$, 200 MHz) δ (ppm): 1–1.5 (m, α-CH$_3$), 2.2–5.1 (m, cellulosic H+benzylic H), 6.7–7.5 (m, aromatic H).

$^{13}$C-NMR (CDCl$_3$, 200 MHz) δ (ppm): 19.2 (s, α-CH$_3$), 45.36 (s, CH$_2$ primary alcohol of the glucose), 62.3 (s, α-CH), 72.17 (m, 4 glucose CH), 99.43 (s, glucose CH), 127.84 128.9 129.46 (s, aromatic CH), 140.11 (s, aromatic C$_{IV}$), 173.8 (s, C=O ester).

Elemental Analysis:
% calculated: C 70.96%, H 6.09% (for a trisubstitution).
% obtained: C 70.81%, H 6.08%.

Optical rotation: [α]$^{20}$=−104.0° (λ=436 nm, c=0.8 g/dm$^3$, CHCl$_3$).

The distribution of the R and S attached acyl units is respectively 62% and 38% (distribution determined by hydrolysis, cf. Example 35).

Example 1A

Comparative Synthesis of Cellulose α-Phenylpropionate in Pyridine (Reaction for 48H at 25° C.):

The process is performed as in Example 1, but carrying out the reaction at 25° C. instead of 115° C. and with 7 equivalents (instead of 8.5) of racemic α-phenylpropionic acid chloride. A cellulose α-phenylpropionate chiral polymer is obtained in a yield of 61% (on the basis of a trisubstitution) with a DS=2.97 determined by elemental analysis. The IR and NMR analyses are identical to those described in Example 1.

Elemental Analysis:
% calculated: C 70.96%, H 6.09% for a trisubstitution
% obtained: C 70.86%, H 6.12%.

The distribution of the R and S attached acyl units is respectively 68% and 32% (distribution determined by hydrolysis, cf. Example 35A).

Example 1B

Comparative Synthesis of Cellulose α-Phenylpropionate in a Pyridine/Triethylamine/DMAP Mixture (Reaction for 48H at 120° C.):

The process is performed as in Example 1, but in the presence of a mixture of pyridine/triethylamine/DMAP (4-(N,N-dimethylamino)-pyridine), the pyridine and the triethylamine being in a proportion of 2/1 (v/v) and the DMAP being in catalytic amount. The reaction is carried out with 7 equivalents (instead of 8.5) of racemic α-phenylpropionic acid chloride. A cellulose α-phenylpropionate chiral polymer is obtained in a yield of 70% (on the basis of a trisubstitution) with a DS=2.96 determined by elemental analysis. The IR and NMR analyses are identical to those described in Example 1.

Elemental Analysis:
% calculated: C 70.96%, H 6.09% (for a trisubstitution).
% obtained: C 70.88%, H 6.12%.

The distribution of the R and S attached ester units is respectively 47% and 53% (distribution determined by hydrolysis, cf. Example 35B).

Example 1C

Comparative Synthesis of Cellulose α-Phenylpropionate in a Pyridine/DABCO/DMAP Mixture (Reaction for 24H at 90° C.):

The process is performed as in Example 1, but in the presence of a mixture of pyridine/DABCO/DMAP, the pyridine and the DABCO (1,4-diazabicyclo[2.2.2]-octane) being in a proportion of 48 ml and 9.6 g, and the DMAP being in catalytic amount. The reaction is carried out with 7 equivalents (instead of 8.5) of racemic α-phenylpropionic acid chloride. A cellulose α-phenylpropionate chiral polymer is obtained in a yield of 31% (on the basis of a trisubstitution) with a DS=2.00 determined by elemental analysis. The IR and NMR analyses are identical to those described in Example 1.

Elemental Analysis:
% calculated: C 70.96%, H 6.09% (for a trisubstitution).
% obtained: C 67.76%, H 5.97%.

The distribution of the R and S attached ester units is respectively 46% and 54% (distribution determined by hydrolysis, cf. Example 35C).

Example 1D

Comparative Synthesis of Cellulose α-Phenylpropionate in 2-Picoline (Reaction for 48H at 115° C.):

The process is performed as in Example 1, but carrying out the reaction in 2-picoline. A cellulose α-phenylpropionate chiral polymer is obtained in a yield of 52% (on the basis of a trisubstitution) with a DS=1.87 determined by elemental analysis. The IR and NMR analyses are identical to those described in Example 1.

Elemental Analysis:
% calculated: C 70.96%, H 6.09% (for a trisubstitution).
% obtained: C 67.24%, H 6.02%.

The distribution of the R and S attached ester units is respectively 43% and 57% (distribution determined by hydrolysis, cf. Example 35D).

Example 1E

Comparative Synthesis of Cellulose α-Phenylpropionate in 4-Picoline (Reaction for 48H at 115° C.):

The process is performed as in Example 1, but carrying out the reaction in 4-picoline. A cellulose α-phenylpropionate chiral polymer is obtained in a yield of 26% (on the basis of a trisubstitution) with a DS=1.13 determined by elemental analysis. The IR and NMR analyses are identical to those described in Example 1.

Elemental Analysis:
% calculated: C 70.96%, H 6.09% (for a trisubstitution).
% obtained: C 62.77%, H 6.34%.

The distribution of the R and S attached ester units is respectively 54% and 46% (distribution determined by hydrolysis, cf. Example 35E).

Example 1F

Comparative Synthesis of Amylopectin α-Phenylpropionate in Pyridine (Reaction for 24H at 100° C.):

0.90 g (5.56 mmol) of glucidex predried overnight under vacuum at 120° C., and 60 ml of pyridine predistilled and dried over KOH are placed in a 100 ml three-necked round-bottomed flask fitted with a condenser on which is mounted a calcium chloride guard tube, a septum and an addition funnel. The mixture is brought to 80° C. and then cooled. Next, 8.42 g (9 eq) of α-phenylpropionic acid chloride are added by syringe and at room temperature to the reaction medium, over 10 min. The mixture is then maintained at reflux at 100° C. for 24 h.

The precooled mixture is poured into 300 ml of MeOH. An amylopectin ester precipitate forms immediately. The precipitate is filtered off and dried and is then dissolved in a minimum amount of $CH_2Cl_2$. The solution in $CH_2Cl_2$ is again added dropwise to 50 ml of MeOH with stirring to obtain a precipitate washed of its impurities. The precipitate, once filtered off and dried for 4 h under vacuum at 25° C., is obtained in the form of a very fine powder: 2.09 g (yield=67% on the basis of a trisubstitution), DS=2.92 determined by elemental analysis.

Analyses:

IR (KBr) $v_{max}$ (cm$^{-1}$): 3100–2800 (—$CH_3$), 1770 (C=O) 1600/1510/700 (para aromatic C=C), 1460 ($\delta_{an}$ $CH_3$), 1170 and 1090 (C=O/C—O).

$^1$H NMR (CDCl$_3$, 200 MHz) δ (ppm): 0.8–1.6 (m, α-$CH_3$), 2.5–5.5 (m, O—$CH_3$+amylopectin H+benzylic H), 6.5–7.5 (m, aromatic H).

Elemental Analysis:
% calculated: C 70.96%, H 6.09% for a trisubstitution
% obtained: C 70.86%, H 6.12%.

The distribution of the R and S attached ester units is respectively 49% and 51% (distribution determined by hydrolysis, cf. Example 35F).

Example 2

Comparative Synthesis of Cellulose α-Phenylpropionate in Triethylamine

The process is performed as in Example 1, but replacing the pyridine with triethylamine; with 0.42 g of cellulose, 3.6 g (9 equivalents) of racemic α-phenylpropionic acid chloride, 40 ml of triethylamine and refluxing at 115° C. The nonesterified initial cellulose is thus obtained (polymer totally insoluble in dichloromethane, IR identical to the initial cellulose).

Example 3

Comparative Synthesis of Cellulose α-Phenylpropionate in Pyridine (Reaction for 24H)

The process is performed as in Example 1, but with a reaction time of 24 h instead of 48 h; with 0.4 g of cellulose, 3.7 g (9 equivalents) of racemic α-phenylpropionic acid chloride, 40 ml of pyridine and refluxing at 115° C. 0.63 g (yield=44.2% on the basis of a trisubstitution) of a cellulose α-phenylpropionate chiral polymer with a degree of substitution of 2.5 determined by elemental analysis is thus obtained.

Analyses:

IR(KBr) $v_{max}$ (cm$^{-1}$): 3500 (OH), 3100–2850 (—$CH_3$), 1760 (—C=O), 1610/1510/710 (para aromatic C=C), 1480 (δas-$CH_3$), 1170 and 1090 (C=O/C—O).

$^1$H NMR (CDCl$_1$, 200 MHz) δ (ppm): 0.8–1.5 (m, α-$CH_3$), 2.2–5.2 (m, cellulosic H+benzylic H), 6.7–7.4 (m, aromatic H).

Elemental Analysis:
% calculated: C 70.96%, H 6.09% (for a trisubstitution).
% obtained: C 69.64%, H 6.08%.

Optical rotation: $[\alpha]^{20}$=−70.0° (λ=436 nm, c=0.7 g/dm$^3$, CHCl$_3$).

The distribution of the R and S attached acyl units is respectively 58% and 42% (distribution determined by hydrolysis, cf. Example 36).

Example 4

Comparative Synthesis of Cellulose α-Phenylpropionate in a Pyridine/Toluene Mixture:

0.4 g (2.5 mmol) of Avicel microcrystalline cellulose (Merck 2331, [(162)n]g on the basis of the glucose monomer), predried overnight at 120° C. in a vacuum oven, and 60 ml of toluene, predistilled and dried over molecular sieves, are placed in a 100 ml three-necked round-bottomed flask fitted with a condenser on which is mounted a calcium chloride guard tube, an addition funnel and a thermometer. The mixture is stirred and heated at 80° C. for one hour. 4 ml of pyridine predistilled and stored over KOH are added. The mixture is cooled to room temperature and 1.3 g (8 mmol, 3 equivalents) of freshly prepared racemic α-phenylpropionic acid chloride mixed with 10 ml of toluene are added dropwise over 10 min. The reaction is maintained at 125° C. for 5 h. The mixture is cooled to room temperature and a further 2.1 g (12 mmol, 5 equivalents) of freshly prepared α-phenylpropionic acid chloride mixed with 10 ml of toluene are added dropwise over 10 min. The reaction is again maintained at 125° C. for 43 h.

After cooling, the reaction mixture is poured into 100 ml of methanol with stirring. The precipitate formed is recovered by filtration and then dissolved in 30 ml of dichloromethane. The solution is filtered and concentrated under reduced pressure. The residue is poured into 100 ml of methanol with stirring and the grafted polymer is recovered, by filtration, in the form of a dark-colored powder. These dissolution-precipitation operations are carried out a second time. The product obtained is dried in a vacuum oven for two hours at 50° C. 1.13 g (yield=80% on the basis of a trisubstitution) of a cellulose α-phenylpropionate chiral polymer with a degree of substitution of 2.5 determined by elemental analysis are obtained.

Analyses:

IR(KBr) $v_{max}$ (cm$^{-1}$): 3500 (OH), 3100–2800 (—$CH_3$) 0.1760 (C=O), 1610/1510/710 (para aromatic C=C), 1480 (δas-$CH_3$), 1170 and 1090 (C=O/C—O).

$^1$H NMR (CDCl$_3$, 200 MHz) δ (ppm): 0.9–1.9 (m, α-$CH_3$), 2.4–5.1 (m, cellulosic H+benzylic H), 6.7–7.5 (m, aromatic H).

Elemental Analysis:
% calculated: C 70.96%, H 6.09% (for a trisubstitution).
% obtained: C 69.51%, H 6.07%.

Optical rotation: $[\alpha]^{20}$=−75.0° (λ=436 nm, c=0.7 g/dm$^3$, CHCl$_3$).

The distribution of the R and S attached acyl units is respectively 58% and 42% (distribution determined by hydrolysis, cf. Example 37).

Example 5

Comparative Synthesis of Cellulose α-Phenylpropionate in a Mixture of Toluene and Triethylamine:

The process is performed as in Example 3, but replacing the pyridine with triethylamine; with 0.41 g of cellulose, 60 ml of toluene, 1.3 g and then 2 g (7 equivalents) of racemic α-phenylpropionic acid chloride mixed with 10 ml of toluene, 5 ml of triethylamine and refluxing at 120° C. The nonesterified initial cellulose is obtained (polymer totally insoluble in dichloromethane, IR identical to the initial cellulose).

Example 6

Synthesis of Cellulose Di-α-Phenylpropionate in Pyridine

The process is performed as in Example 1, but at a reaction temperature of 90° C. instead of 115° C., with three equivalents of racemic α-phenylpropionic acid chloride instead of eight and by carrying out ultrasonic agitation for 30 min at the time of dissolution of the phase in dichloromethane (0.6 g of cellulose, 1.9 g (three equivalents) of racemic α-phenylpropionic acid chloride, 45 ml of pyridine, heating at 90° C.). 0.93 g (yield=58.9% on the basis of a disubstitution) of a cellulose α-phenylpropionate chiral polymer with a degree of substitution of 1.99 determined by elemental analysis is thus obtained.

Analyses:

IR(KBr) $v_{max}$ (cm$^{-1}$): 3530–2900 (OH), 3100–2800 (—CH$_3$), 1760 (C=O), 1610/1510/700 (para aromatic C=C), 1480 (δas-CH$_3$), 1170 and 1090 (C=O/C—O).

$^1$H NMR (CDCl$_3$, 200 MHz) δ (ppm): 0.9–1.8 (m, α-CH$_3$), 2.5–5.3 (m, cellulosic H+benzylic H+residual OH), 6.7–7.4 (m, aromatic H).

Elemental Analysis:

% calculated: C 67.6%, H 6.1% (for a disubstitution).
% obtained: C 67.56%, H 6.1%.

The optical rotation was not measured on account of the insufficient solubility of the polymer in CHCl$_3$.

The distribution of the R and S attached acyl units is respectively 60% and 40% (distribution determined by hydrolysis, cf. Example 38).

Example 7

Synthesis of Cellulose Mono-α-Phenylpropionate in Pyridine 0.92 g (5.7 mmol) of Avicel microcrystalline cellulose (Merck 2331, M=[(162)n]g on the basis of the glucose monomer), predried overnight at 120° C. in a vacuum oven, and 40 ml of pyridine, predistilled and placed over KOH, are placed in a 100 ml three-necked round-bottomed flask fitted with a condenser on which is mounted a calcium chloride guard tube, an addition funnel and a thermometer. The mixture is stirred and heated at 80° C. for 1 hour. The mixture is cooled to room temperature and 1.7 g (11 mmol, 1.8 equivalents) of freshly prepared racemic α-phenylpropionic acid chloride are added dropwise. The reaction is maintained at 90° C. for 48 h.

The reaction mixture is poured into 50 ml of methanol with stirring. The precipitate formed is recovered by filtration and is then agitated by ultrasound for 15 min in 50 ml of dichloromethane. The solution is filtered on paper and concentrated under reduced pressure. The residue is poured into 50 ml of methanol with stirring and a beige-colored grafted polymer is recovered by filtration. These dissolution-filtration-precipitation operations are carried out a second time with an intermediate filtration of the dichloromethane solution being carried out on a paper of finer porosity. The product obtained is dried in a vacuum oven for two hours at 50° C. 1136 g (yield=68% on the basis of a monosubstitution) of a cellulose α-phenylpropionate chiral polymer with a degree of substitution of 0.91 determined by elemental analysis are obtained.

Analyses:

IR(KBr) $v_{max}$ (cm$^{-1}$): 3600–3200 (OH), 3020–2800 (—CH$_3$), 1760 (C=O), 1610/1510/710 (para aromatic C=C), 1470 (δas-CH$_3$), 1170 and 1090 (C=O/C—O).

$^1$H NMR (d$_5$-pyridine, 200 MHz) δ (ppm): 1–2 (m, α-CH$_3$), 3–6 (m, cellulosic H+benzylic H+residual OH), 7–8 (m, aromatic H).

Elemental Analysis:

% calculated: C 61.2%, H 6.12% (for a disubstitution).
% obtained: C 60.36%, H 6.1%.

The optical rotation was not measured on account of the poor solubility of the polymer in CHCl$_3$.

The distribution of the R and S attached acyl units is respectively 58% and 42% (distribution determined by hydrolysis, cf. Example 39).

Example 8

Synthesis of Amylose α-Phenylpropionate in Pyridine

The process is performed as in Example 1, but replacing the cellulose with amylose B (Nacalaï Tesque Mw=16000); with 0.4 g of amylose, 2.9 g (7 equivalents) of racemic α-phenylpropionic acid chloride, 40 ml of pyridine and refluxing at 115° C. for 50 h. 0.887 g (yield=64.4% on the basis of a trisubstitution) of an amylose α-phenylpropionate chiral polymer with a degree of substitution of 3 determined by elemental analysis is thus obtained.

Analyses:

IR(KBr) $v_{max}$ (cm$^{-1}$): 3100–2800 (—CH$_3$), 1760 (C=O), 1610/1500/700 (para aromatic C=C), 1480 (δas-CH$_3$) 1170 and 1090 (C=O/C—O).

$^1$H NMR (CDCl$_3$, 200 MHz) δ (ppm): 0.7–1.8 (m, α-CH$_3$), 2.8–5.5 (m, cellulosic H+benzylic H), 6.6–7.6 (m, aromatic H).

Elemental Analysis:

% calculated: C 70.96%, H 6.09% (for a trisubstitution).
% obtained: C 70.95%, H 6.09%.

Optical rotation: $[\alpha]^{20}$=113.0° (λ=436 nm, c=1 g/dm$^3$, CHCl$_3$).

The distribution of the R and S attached acyl units is respectively 53% and 47% (distribution determined by hydrolysis, cf. Example 40).

Example 9

Synthesis of β-Cyclodextrin α-Phenylpropionate in Pyridine

The process is performed as in Example 1, but replacing the cellulose with β-cyclodextrin (from Roquette, M=[(162)n]g, batch E. 0113); with 0.374 g of β-cyclodextrin, 3.5 g (9 equivalents) of racemic α-phenylpropionic acid chloride, 40 ml of pyridine and refluxing at 115° C. for 18 h. 0.432 g (yield=33.5% based on a trisubstition) of a β-cyclodextrin α-phenylpropionate chiral polymer with a degree of substitution of 2.9 determined by elemental analysis is thus obtained.

Analyses:

IR(KBr) $v_{max}$ (cm$^{-1}$): 3100–2800 (—CH$_3$), 1770 (C=O), 1600/1510/700 (para aromatic C=C), 1460 (δas-CH$_3$), 1170 and 1090 (C=O/C—O).

$^1$H NMR (CDCl$_3$, 200 MHz) δ (ppm): 0.8–2 (m, α-CH$_3$), 2.7–5.4 (m, cellulosic H+benzylic H), 6.5–7.8 (m, aromatic H).

Elemental Analysis:

% calculated: C 70.96%, H 6.09% (for a trisubstitution).

% obtained: C 70.80%, H 6.10%.

Optical rotation: $[\alpha]^{20}$=+77.8° (λ=436 nm, c=1.6 g/dm$^3$, CHCl$_3$).

Example 10

Synthesis of Cellulose α-(p-Chlorophenyl)Propionate in Pyridine

0.4 g (2.5 mmol) of Avicel microcrystalline cellulose (Merck 2331, M=[(162)n]g on the basis of the glucose monomer), predried overnight at 120° C. in a vacuum oven, and 40 ml of pyridine, predistilled and placed over KOH, are placed in a 100 ml three-necked round-bottomed flask fitted with a condenser on which is mounted a calcium chloride guard tube, an addition funnel and a thermometer. The mixture is stirred and heated at 80° C. for one hour. The mixture is cooled to room temperature and 3.3 g (18 mmol, 7 equivalents) of freshly prepared racemic α-(p-chlorophenyl)propionic acid chloride are added dropwise. The reaction is maintained at 115° C. for 30 h.

After cooling, 40 ml of dichloromethane and 20 ml of saturated Na$_2$CO$_3$ solution are added to the reaction mixture. The mixture is stirred for 15 min and the organic phase and the aqueous phase are separated after settling has taken place. The organic phase is washed with 10 ml of water, dried with MgSO$_4$ and then concentrated under reduced pressure to give a solution of about 5 to 10 ml. This solution is poured into 50 ml of methanol with stirring and the precipitate formed is recovered by filtration. The polymer is dissolved in 30 ml of dichloromethane; this solution is then filtered and concentrated under reduced pressure. The residue is poured into 50 ml of methanol with stirring and a dark-colored grafted polymer is recovered by filtration. These dissolution-precipitation operations are carried out a second time. The product obtained is dried in a vacuum oven for two hours at 50° C. 1.56 g (yield=95.5% on the basis of a trisubstitution) of a cellulose α-(p-chlorophenyl)propionate chiral polymer with a degree of substitution of 3 determined by elemental analysis are obtained.

Analyses:

IR(KBr) $v_{max}$ (cm$^{-1}$): 3000–2800 (—CH$_3$), 1760 (C=O), 1600/1500/780 (para-disubstituted aromatic C=C), 1480 (δas-CH$_3$), 1170 and 1090 (C=O/C—O), 810 (C—Cl).

$^1$H NMR (CDCl$_3$, 200 MHz) δ (ppm): 0.8–1.8 (m, α-CH$_3$), 2.2–5.2 (m, cellulosic H+benzylic H), 6.6–7.6 (m, aromatic H).

Elemental Analysis:

% calculated: C 59.86%, H 4.68% (for a trisubstitution).

% obtained: C 59.86%, H 4.68%.

Optical rotation: $[\alpha]^{20}$=−63.0° (λ=436 nm, c=2.05 g/dm$^3$, CHCl$_3$).

The distribution of the R and S attached acyl units is respectively 56% and 44% (distribution determined by hydrolysis, cf. Example 41).

Example 11

Synthesis of Cellulose Mono-α(p-Chlorophenyl)Propionate in Pyridine

The process is performed as in Example 7, but replacing the α-phenylpropionic acid with α-(p-chlorophenyl)propionic acid; with 0.92 g of cellulose, 1.9 g (1.8 equivalents) of racemic α-(p-chlorophenyl)propionic acid chloride, 40 ml of pyridine and heating at 90° C. 1679 g (yield=90% on the basis of a monosubstitution) of a cellulose mono-α-(p-chlorophenyl)propionate chiral polymer with a degree of substitution of 0.96 determined by elemental analysis are thus obtained.

Analyses:

IR(KBr) $v_{max}$ (cm$^{-1}$) 3800–3100 (OH), 3000–2800 (—CH$_3$), 1760 (C=O), 1600/1500/780 (para-disubstituted aromatic C=C), 1480 (δas-CH$_3$), 1170 and 1090 (C=O/C—O) cm$^{-1}$, 850 (C—Cl).

$^1$H NMR (d$_5$-pyridine, 200 MHz) δ (ppm): 1–2 (m, α-CH$_3$), 3–6 (m, cellulosic H+benzylic H+residual OH), 7–7.9 (m, aromatic H).

Elemental Analysis:

% calculated: C 54.79%, H 5.17% (for a disubstitution).

% obtained: C 54.57%, H 5%.

The optical rotation was not measured on account of the poor solubility of the polymer in CHCl$_3$.

Example 12

Synthesis of Cellulose Mono-α-(p-Chlorophenyl)Propionate in Pyridine

The process is performed as in Example 11, with 1 g of cellulose, 1.3 g (1.15 equivalents) of racemic α-(p-chlorophenyl)propionic acid chloride, 40 ml of pyridine and heating at 90° C. 1603 g (yield=79.1% on the basis of a monosubstitution) of a cellulose mono-α-(p-chlorophenyl) propionate chiral polymer with a degree of substitution of 0.6 determined by elemental analysis are thus obtained.

Analyses:

IR(KBr) $v_{max}$ (cm-1): 3700–3100 (OH), 3000–2800 (—CH3), 1760 (C=O), 1600/1500/780 (para-disubstituted aromatic C=), 1480 (δas-CH3), 1170 and 1090 (C=O/C—O), 840 (C—Cl).

$^1$H NMR (d$_5$-pyridine, 200 MHz) δ (ppm): 1–2 (m, α-CH$_3$), 3–6 (m, cellulosic H+benzylic H+residual OH), 7–7.9 (m, aromatic H).

Elemental Analysis:

% calculated: C 54.79%, H 5.17% (for a disubstitution).

% obtained: C 52.26%, H 4.89%.

The optical rotation could not be measured on account of the poor solubility of the polymer in $CHCl_3$.

Example 13

Synthesis of Amylose
α-(p-Chlorophenyl)-Propionate in Pyridine

The process is performed as in Example 10, but replacing the cellulose with amylose B (Nacalaï Tesque Mw=16000); with 0.5 g of cellulose, 3.3 g (five equivalents) of racemic α-(p-chlorophenyl)propionic acid chloride, 40 ml of pyridine and refluxing at 115° C. for 30 h. 1.95 g (yield=98% on the basis of a trisubstitution) of a cellulose α-(p-chlorophenyl)-propionate chiral polymer with a degree of substitution of 3 determined by elemental analysis are thus obtained.

Analyses:

IR(KBr) $v_{max}$ ($cm^{-1}$): 3000–2900 (—$CH_3$), 1760 (C=O) 1600/1500/760 (para-disubstituted aromatic C=C), 1480 (δas-$CH_3$), 1170 and 1090 (C=O/C—O), 820 (C—Cl).

$^1H$ NMR ($CDCl_3$, 200 MHz) δ (ppm): 0.8–1.9 (m, α-$CH_3$), 2.5–5.3 (m, cellulosic H+benzylic H), 6.6–7.6 (m, aromatic H).

Elemental Analysis:

% calculated: C 59.86%, H 4.68% (for a trisubstitution).

% obtained: C 59.86%, H 4.65%.

OPTICAL ROTATION: $[\alpha]^{20}$=90.0° (λ=436 nm, c=1.58 g/$dm^3$, $CHCl_3$).

The distribution of the R and S attached acyl units is respectively 52% and 48% (distribution determined by hydrolysis, cf. Example 44).

Example 14

Synthesis of Cellulose Ketoprofenate in Pyridine 0.295 g (1.8 mmol) of Avicel microcrystalline cellulose (Merck 2331, M=[(162)n]g on the basis of the glucose monomer), predried overnight at 120° C. in a vacuum oven, and 50 ml of pyridine, predistilled and placed over KOH, are placed in a 100 ml three-necked round-bottomed flask fitted with a condenser on which is mounted a calcium chloride guard tube, an addition funnel and a thermometer. The mixture is stirred and heated at 80° C. for one hour. The mixture is cooled to room temperature and 4.85 g (18 mmol, 10 equivalents) of freshly prepared racemic ketoprofen chloride are added dropwise. The reaction is maintained at 90° C. for 22 h and then at 120° C. for 40 h.

After cooling, the reaction mixture is poured into 100 ml of methanol with stirring. The precipitate formed is recovered by filtration and then dissolved in 50 ml of dichloromethane. The solution is filtered and concentrated under reduced pressure. The residue is poured into 100 ml of methanol with stirring and a dark-colored grafted polymer is recovered by filtration. These dissolution-precipitation operations are carried out a second time. The product obtained is dried in a vacuum oven for two hours at 50° C. 0.68 g (yield=43% on the basis of a trisubstitution) of a cellulose ketoprofenate chiral polymer with a degree of substitution of 2.35 determined by elemental analysis is obtained.

Analyses:

IR(KBr) $v_{max}$ ($cm^{-1}$): 3500 (OH), 3000–2900 (—$CH_3$) 1760 (ester C=O), 1680 and 1300 (ketone C=O), 1610/1590/780 (aromatic C=C), 1480 (δas-$CH_3$), 1170 and 1080 (C=O/C—O).

$^1H$ NMR ($CDCl_3$, 200 MHz) δ (ppm): 0.8–1.5 (m, α-$CH_3$), 2.3–5.3 (m, cellulosic H+benzylic H), 7–7.8 (broad multiplet, aromatic H).

Elemental Analysis:

% calculated: C 74.48%, H 5.28% (for a trisubstitution).

% obtained: C 73.00%, H 5.33%.

Optical rotation: $[\alpha]^{20}$=−64.00 (λ=436 nm, c=1.5 g/$dm^3$, $CHCl_3$).

The distribution of the R and S attached acyl units is respectively 58% and 42% (distribution determined by hydrolysis, cf. Example 45).

Example 15

Comparative Synthesis of Cellulose Ketoprofenate
in a Pyridine/Triethylamine/DMAP Mixture 0.5 g (3.1 mmol) of Avicel microcrystalline cellulose (Merck 2331, M=[(162)n]g on the basis of the glucose monomer), predried overnight at 120° C. in a vacuum oven, and a mixture: pyridine (20 ml, predistilled and placed over KOH)/triethylamine (10 ml, freshly distilled)/DMAP (a few mg) are placed in a 100 ml three-necked round-bottomed flask fitted with a condenser on which is mounted a calcium chloride guard tube, an addition funnel and a thermometer. The mixture is stirred and heated at 80° C. for one hour. It is cooled to 0° C. and 5 g (18.3 mmol, 6 equivalents) of freshly prepared racemic ketoprofen chloride are added dropwise. The reaction is maintained at 120° C. for 20 h.

After cooling, the reaction mixture is poured into 100 ml of methanol with stirring. The precipitate formed is recovered by filtration and then dissolved in 50 ml of dichloromethane. The solution is filtered and concentrated under reduced pressure. The residue is poured into 100 ml of methanol with stirring and a dark-colored grafted polymer is recovered by filtration. These dissolution/precipitation operations are carried out a second time. The product obtained is dried in a vacuum oven at 50° C. for two hours. 0.56 g (yield=21% based on a trisubstitution) of a cellulose ketoprofenate chiral polymer with a degree of substitution of 2.9 determined by elemental analysis is obtained.

Analyses:

IR(KBr) $v_{max}$ ($cm^{-1}$): 3500 (OH), 3000–2900 (—$CH_3$) 1760 (ester C=O), 1680 and 1300 (ketone C=O), 1610/1590/750 (aromatic C=C), 1480 (δas-$CH_3$), 1170 and 1080 (C=O/C—O).

$^1H$ NMR ($CDCl_3$, 200 MHz) δ (ppm): 0.9–1.9 (m, α-$CH_3$), 2.3–5.3 (m, cellulosic H+benzylic H), 6.9–8.2 (broad multiplet, aromatic H).

Elemental Analysis:

% calculated: C 74.48%, H 5.28% (for a trisubstitution).

% obtained: C 74.38%, H 5.30%.

Optical rotation: $[\alpha]^{20}$=−80.0° (λ=436 nm, c=1 g/$dm^3$, $CHCl_3$).

The distribution of the R and S attached acyl units is respectively 49.5% and 50.5% (distribution determined by hydrolysis, cf. Example 46).

Example 16

Synthesis of Amylose Ketoprofenate in Pyridine

The process is performed as in Example 14, but replacing the cellulose with amylose B (Nacalaï Tesque Mw=16000); with 0.199 g of cellulose, 2.85 g (8.5 equivalents) of racemic ketoprofen chloride, 40 ml of pyridine and heating at 90° C. for 20 h and then at 115° C. for 44 h. 0.416 g (yield=42.9% on the basis of a trisubstitution) of an amylose ketoprofenate chiral polymer with a degree of substitution of 2.42 determined by elemental analysis is thus obtained.

Analyses:

IR(KBr) $v_{max}$ (cm$^{-1}$): 3500 (OH), 3050–2950 (—CH$_3$) 1760 (ester C=O), 1680 and 1300 (ketone C=O), 1610/1590/770 (aromatic C=C), 1470 ($\delta$as-CH$_3$), 1170 and 1080 (C=O/C—O).

$^1$H NMR (CDCl$_3$, 200 MHz) $\delta$ (ppm): 0.9–1.9 (m, $\alpha$-CH$_3$), 2.3–5.3 (m, cellulosic H+benzylic H), 7–8.3 (broad multiplet, aromatic H).

Elemental Analysis:

% calculated: C 74.48%, H 5.28% (for a trisubstitution).
% obtained: C 73.28%, H 5.33%.

Optical rotation: $[\alpha]^{20}$=−90.0° ($\lambda$=436 nm, c=0.5 g/dm$^3$, CHCl$_3$).

The distribution of the R and S attached acyl units is respectively 51% and 49% (distribution determined by hydrolysis, cf. Example 47).

Example 17

Synthesis of Cellulose Monoketoprofenate in Pyridine

The process is performed as in Example 7, but replacing the $\alpha$-phenylpropionic acid with ketoprofen and carrying out the reaction at room temperature; with 1 g of cellulose, 2.4 g (1.45 equivalents) of racemic ketoprofen chloride, 40 ml of pyridine, at 25° C. for 60 h. 2.09 g (yield=85.2% on the basis of a monosubstitution) of a cellulose monoketoprofenate chiral polymer with a degree of substitution of 1 determined by elemental analysis are thus obtained.

Analyses:

IR(KBr) $v_{max}$ (cm$^{-1}$): 3500–3200 (OH), 3000–2800 (—CH$_3$), 1760 (ester C=O), 1680 and 1290 (ketone C=O), 1610/1590/770 (aromatic C=C), 1480 ($\delta$as-CH$_3$) 1170 and 1080 (C=O/C—O).

$^1$H NMR (d$_5$-pyridine, 200 MHz) $\delta$ (ppm): 1–2 (m, $\alpha$-CH$_3$), 2.3–5.3 (m, cellulosic H+benzylic H+residual OH), 7–7.8 (broad multiplet, aromatic H).

Elemental Analysis:

% calculated: C 66.33%, H 5.53% (for a monosubstitution),
% obtained: C 66.30%, H 5.35%.

The optical rotation was not measured due to the poor solubility of the polymer in CHCl$_3$.

The distribution of the R and S attached acyl units is respectively 55% and 45% (distribution determined by hydrolysis, cf. Example 48).

Example 18

Synthesis of Cellulose Ibuprofenate in Pyridine

The process is performed as in Example 1, but replacing the $\alpha$-phenylpropionic acid with ibuprofen; with 0.383 g of cellulose, 5 g (9.5 equivalents) of racemic ibuprofen chloride, 40 ml of pyridine and refluxing at 115° C. 1.207 g (yield=70.3% on the basis of a trisubstitution) of a cellulose ibuprofenate chiral polymer with a degree of substitution of 2.73 determined by elemental analysis are thus obtained.

Analyses:

IR(KBr) $v_{max}$ (cm$^{-1}$): 3500 (OH), 3000–2800 and 1420 (—CH$_3$, —CH$_2$), 1760 (ester C=O), 1500/820 (aromatic C=C), 1480 ($\delta$as-CH$_3$), 1170 and 1090 (C=O/C—O).

$^1$H NMR (CDCl$_3$, 200 MHz) $\delta$ (ppm): 0.8 (m, (CH$_3$)$_2$—CH), 1.1–1.4 (m, $\alpha$-CH$_3$), 1.9 (m, (CH$_3$)$_2$—CH), 2.4 (m, CH$_2$—CH), 3.1–5 (m, cellulosic H+benzylic H), 6.8–7.2 (m, aromatic H).

Elemental Analysis:

% calculated: C 74.38%, H 7.99% (for a trisubstitution).
% obtained: C 73.73%, H 8.10%.

Optical rotation: $[\alpha]^{20}$=−81.0° ($\lambda$=436 nm, c=1 g/dm$^3$, CHCl$_3$).

The distribution of the R and S attached acyl units is respectively 63% and 37% (distribution determined by hydrolysis, cf. Example 49).

Example 18A

Synthesis of Cellulose Ibuprofenate in a Pyridine/Triethylamine/DMAP Mixture (Reaction for 48H at 115° C.)

The process is performed as in Example 18, but in the presence of a mixture of pyridine/triethylamine/DMAP, the pyridine and triethylamine being in a 2/1 (v/v) proportion and the DMAP being in catalytic amount. A cellulose ibuprofenate chiral polymer is thus obtained in a yield of 51% (on the basis of a trisubstitution) and with a degree of substitution of 2.77 determined by elemental analysis.

The IR and NMR analyses are identical to those described in Example 18.

Elemental Analysis:

% calculated: C 74.38%, H 7.99% (for a trisubstitution).
% obtained: C 73.83%, H 8.02%.

The distribution of the R and S attached ester units is respectively 47% and 53% (distribution determined by hydrolysis, cf. Example 49A).

Example 19

Synthesis of $\beta$-Cyclodextrin Ibuprofenate in Pyridine

The process is performed as in Example 10, but replacing the $\alpha$-(p-chlorophenyl)propionic acid with ibuprofen and the cellulose with $\beta$-cyclodextrin; with 0.5 g of $\beta$-cyclodextrin, 4 g (5.8 equivalents) of racemic ibuprofen chloride, 40 ml of pyridine and refluxing at 120° C. for 18 h. 0.48 g (yield=1.5% on the basis of a trisubstitution) of a $\beta$-cyclodextrin ibuprofenate chiral polymer with a degree of substitution of 2.9 determined by elemental analysis is thus obtained.

Analyses:

IR(KBr) $v_{max}$ (cm$^{-1}$): 3000–2800 and 1390 (—CH$_3$, —CH$_2$), 1760 (ester C=O), 1530/820 (aromatic C=C), 1480 ($\delta$as-CH$_3$), 1170 and 1090 (C=O/C—O).

$^1$H NMR (CDCl$_3$, 200 MHz) $\delta$ (ppm): 0.9 (m, (CH$_3$)$_2$—CH), 1.1–1.6 (m, $\alpha$-CH$_3$), 1.9 (m, (CH$_3$)$_2$—CH), 2.4 (m, CH$_2$—CH), 2.9–5.5 (m, cellulosic H+benzylic H), 6.5–7.3 (m, aromatic H).

Elemental Analysis:
% calculated: C 74.38%, H 7.99% (for a trisubstitution).
% obtained: C 73.30%, H 8.05%.
Optical rotation: $[\alpha]^{20}$=+158.2° ($\lambda$=436 nm, c=3.3 g/dm$^3$, CHCl$_3$).

Example 20

Synthesis of Cellulose
α-(3,5-Dimethylphenyl)Propionate in Pyridine

The process is performed as in Example 14, but replacing the ketoprofen with 3,5-dimethylphenylpropionic acid; with 0.25 g of cellulose, 2.73 g (9 equivalents) of racemic 3,5-dimethylphenylpropionic acid chloride, 40 ml of pyridine, heating at 90° C. for 24 h and then at 120° C. for 20 h and ultrasonic agitation during the dissolution of the phase in dichloromethane at the time of purification. 0.447 g (yield=45.1% on the basis of a trisubstitution) of a cellulose 3,5-dimethylphenylpropionate chiral polymer with a degree of substitution of 1.74 determined by elemental analysis is thus obtained.

Analyses:
IR(KBr) $v_{max}$ (cm$^{-1}$): 3500–3400 (OH), 3000–2900 (—CH$_3$), 1760 (ester C=O), 1600/800 (symmetrical trisubstituted aromatic C=C), 1470 ($\delta$as-CH$_3$), 1170 and 1090 (C=O/C—O).
$^1$H NMR (d$_5$-pyridine, 200 MHz) $\delta$ (ppm): 1.1–2 (m, α-CH$_3$), 2.1–2.8 (m, 2*CH$_3$—Ar), 3–6 (m, cellulosic H+benzylic H), 6.8–7.5 (m, aromatic H).
Elemental Analysis:
% calculated: C 72.9%, H 7.17% (for a trisubstitution).
% obtained: C 68.5%, H 6.63%.
The optical rotation was not measured due to the poor solubility of the polymer in CHCl$_3$.
The distribution of the R and S attached acyl units is respectively 58% and 42% (distribution determined by hydrolysis, cf. Example 50).

Example 21

Synthesis of Cellulose
α-(3,5-Dimethylphenyl)Propionate in Pyridine+DMAP

The process is performed as in Example 20, but adding a few mg of DMAP to the pyridine; with 0.21 g of cellulose, 2.34 g (9 equivalents) of racemic 3,5-dimethylphenylpropionic acid chloride, 40 ml of pyridine+a few mg of DMAP, heating at 90° C. for 24 h and then at 120° C. for 44 h. 0.613 g (yield=73.7% on the basis of a trisubstitution) of a cellulose 3,5-dimethylphenylpropionate chiral polymer with a degree of substitution of 3 determined by elemental analysis is thus obtained.

Analyses:
IR(KBr) $v_{max}$ (cm$^{-1}$): 3000–2800 (—CH$_3$), 1760 (ester C=O), 1610/810 (symmetrical trisubstituted aromatic C=C), 1470 ($\delta$as-CH$_3$), 1170 and 1090 (C=O/C—O).
$^1$H NMR (CDCl$_3$, 200 MHz) $\delta$ (ppm): 1–1.8 (m, α-CH$_3$), 2.1–2.8 (m, 2*CH$_3$—Ar), 2.7–5.4 (m, cellulosic H+benzylic H), 6.4–7.2 (m, aromatic H).
Elemental Analysis:
% calculated: C 72.90%, H 7.17% (for a trisubstitution).
% obtained: C 72.98%, H 7.18%.
Optical rotation: $[\alpha]^{20}$=−87.0° ($\lambda$=436 nm, c=1.5 g/dm$^3$, CHCl$_3$).

The distribution of the R and S attached acyl units is respectively 63% and 37% (distribution determined by hydrolysis, cf. Example 51).

Example 22

Synthesis of Cellulose
α-(p-Methylphenyl)Propionate in Pyridine

The process is performed as in Example 20, but replacing the 3,5-dimethylphenylpropionic acid with p-methylphenylpropionic acid; with 0.18 g of cellulose, 1.82 g (9 equivalents) of racemic p-methylphenylpropionic acid chloride, 30 ml of pyridine, heating at 90° C. for 24 h and then at 120° C. for 45 h. 0.491 g (yield=74% on the basis of a trisubstitution) of a cellulose p-methylphenylpropionate chiral polymer with a degree of substitution of 3 determined by elemental analysis is thus obtained.

Analyses:
IR(KBr) vmax (cm$^{-1}$): 3000–2800 (—CH3), 1760 ester C=O), 1550/800 (disubstituted aromatic C=C), 1480 ($\delta$as-CH3), 1170 and 1090 (C=O/C—O).
$^1$H NMR: (CDCl$_3$, 200 MHz) $\delta$ (ppm)=0.9–1.6 (m, α-CH$_3$), 2–2.5 (m, CH$_3$—Ar), 2.7–5.4 (m, cellulosic H+benzylic H), 6.6–7.2 (m, aromatic H).
Elemental Analysis:
% calculated: C 72.00%, H 6.67% (for a trisubstitution).
% obtained: C 72.01%, H 6.68%.
Optical rotation: $[\alpha]^{20}$=−110.0° ($\lambda$=436 nm, c=1.5 g/dm$^3$, CHCl$_3$).

The distribution of the R and S attached acyl units is respectively 62% and 38% (distribution determined by hydrolysis, cf. Example 52).

Example 23

Synthesis of Cellulose α-(2-Thiophenyl)-Propionate
in Pyridine 0.158 g (1 mmol) of Avicel microcrystalline cellulose (Merck 2331, M=[(162)n]g on the basis of the glucose monomer), predried overnight at 120° C. in a vacuum oven, and 40 ml of pyridine, predistilled and placed over KOH, are placed in a 100 ml three-necked round-bottomed flask fitted with a condenser on which is mounted a calcium chloride guard tube, an addition funnel and a thermometer. The mixture is stirred and heated at 80° C. for one hour. The mixture is cooled to room temperature and 1.53 g (9 mmol, 9 equivalents) of freshly prepared racemic 2-thiophenylpropionic acid chloride are added dropwise. During the addition, the chloride reacts very rapidly on contact with even the pyridine vapors. The reaction is left at room temperature for 22 h and then maintained at 90° C. for 48 h.

After cooling, the reaction mixture is poured into 100 ml of methanol with stirring. The precipitate formed is recovered by filtration and then dissolved with ultrasonic agitation in 50 ml of dichloromethane. The solution is filtered through a No. 4 sinter funnel to remove the particles in solid form and is concentrated under reduced pressure. The residue is poured into 100 ml of methanol with stirring and a dark-colored grafted polymer is recovered by filtration. These dissolution-precipitation operations are carried out a second time. The product obtained is dried in a vacuum oven for two hours at 50° C. 0.159 g (yield=27.2% on the basis of a trisubstitution) of a cellulose 2-thiophenylpropionate chiral polymer with a degree of substitution of 1.98 determined by elemental analysis is obtained.

Analyses:

IR(KBr) $v_{max}$ (cm$^{-1}$): 3500–3400 (OH), 3000–2900 (—CH$_3$), 1760 (ester C=O), 1460 ($\delta$as-CH$_3$), 1170 and 1090 (C=O/C—O), 700 (C—S).

$^1$H NMR (CDCl$_3$, 200 MHz) $\delta$ (ppm): 1–1.9 (m, $\alpha$-CH$_3$), 3.2–5.5 (m, cellulosic H+benzylic H), 6.5–7.5 (broad multiplet, heterocyclic H).

Elemental Analysis:

% calculated: C 56.25%, H 4.86% (for a trisubstitution).

% obtained: C 54.73%, H 5.03%.

The polymer is not soluble enough in CHCl$_3$ to be able to measure an optical rotation.

The distribution of the R and S attached acyl units is respectively 50% and 50% (distribution determined by hydrolysis, cf. Example 53).

Example 24

Synthesis of Cellulose $\alpha$-(2-Thiophenyl)-Propionate in Pyridine

The process is performed as in Example 23, but leaving the reaction at room temperature; with 0.185 g of cellulose, 2 g (9 equivalents) of racemic 2-thiophenylpropionic acid chloride, 30 ml of pyridine, 48 h at room temperature. 0.324 g (yield=47.3% on the basis of a trisubstitution) of a cellulose 2-thiophenylpropionate chiral polymer with a degree of substitution of 2.85 determined by elemental analysis is thus obtained.

Analyses:

IR(KBr) $v_{max}$ (cm$^{-1}$): 3000–2900 (—CH$_3$), 1760 (ester C=O), 1470 ($\delta$as-CH$_3$), 1170 and 1090 (C=O/C—O), 700 (C—S).

$^1$H NMR (CDCl$_3$, 200 MHz) $\delta$ (ppm): 1–2 (m, 9H, $\alpha$-CH$_3$), 2.7–5.3 (m, cellulosic H+benzylic H), 6.3–7.3 (broad multiplet, heterocyclic H).

Elemental Analysis:

% calculated: C 56.25%, H 4.86% (for a trisubstitution).

% obtained: C 56.09%, H 4.87%.

Optical rotation: [$\alpha$]$^{20}$=–78.0° ($\lambda$=436 nm, c=0.5 g/dm$^3$, CHCl$_3$).

The distribution of the R and S attached acyl units is respectively 54% and 46% (distribution determined by hydrolysis, cf. Example 54).

Example 25

Synthesis of a Mixed Cellulose Ester of $\alpha$-Phenylpropionic Acid and of Ketoprofen (with Intermediate Purification And Analyses)

❶Synthesis of a Cellulose $\alpha$-Phenylpropionate of DS=0.6:

The process is performed as in Example 7, but with 1.2 equivalents of racemic $\alpha$-phenylpropionic acid chloride instead of 1.8; with 0.9 g of cellulose, 1.1 g (1.2 equivalents) of racemic $\alpha$-phenylpropionic acid chloride, 40 ml of pyridine and heating at 90° C. for 48 h. 1.3 g (yield=79.6% on the basis of a monosubstitution) of a cellulose $\alpha$-phenylpropionate chiral polymer with a degree of substitution of 0.6 determined by elemental analysis are thus obtained.

Analyses:

IR(KBr) $v_{max}$ (cm$^{-1}$): 3600–3200 (OH), 3000–2800 (—CH$_3$) 1760 (C=O), 1600/1500/700 (para aromatic C=C), 1450 ($\delta$as-CH$_3$), 1170 and 1090 (C=O/C—O).

$^1$H NMR (d$_5$-pyridine, 200 MHz) $\delta$ (ppm): 1–2 (m, $\alpha$-CH$_3$), 3–6 (m, cellulosic H+benzylic H+residual OH), 7–8 (m, aromatic H).

Elemental Analysis:

% calculated: C 61.20%, H 6.12% (for a disubstitution).

% obtained: C 56.81%, H 5.84%.

The optical rotation was not measured due to the poor solubility of the polymer in CHCl$_3$.

The distribution of the R and S attached acyl units is 55% and 45% respectively for the acyl units derived from $\alpha$-phenylpropionic acid (distribution determined by hydrolysis, cf. Example 55).

The distribution of the R and S attached acyl units is 54% and 46% respectively for the acyl units derived from ketoprofen (distribution determined by hydrolysis, cf. Example 55).

❷Synthesis of the Mixed Ester by Adding 4 Equivalents of Ketoprofen Chloride to the Preceding Phase:

0.5 g (2 mmol) of cellulose $\alpha$-phenylpropionate chiral polymer with a DS=0.6 and 40 ml of pyridine, predistilled and placed over KOH, are placed in a 100 ml three-necked round-bottomed flask fitted with a condenser on which is mounted a calcium chloride guard tube, an addition funnel and a thermometer. The mixture is stirred and heated at 60° C. for 20 min to dissolve the phase. The mixture is cooled to room temperature and 2.2 g (8 mmol, 4 equivalents) of freshly prepared racemic ketoprofen chloride are added dropwise. The reaction is maintained at 105° C. for 48 h.

After cooling, the reaction mixture is poured into 100 ml of methanol with stirring. The precipitate formed is recovered by filtration and then dissolved in 30 ml of dichloromethane. The solution is filtered and concentrated under reduced pressure. The residue is poured into 100 ml of methanol with stirring and a dark-colored grafted polymer is recovered by filtration. These dissolution-precipitation operations are carried out a second time. The product obtained is dried in a vacuum oven for two hours at 50° C. 1.227 g (yield=30% on the basis of a polymer of DS=0.6 for $\alpha$-phenylpropionic acid and of DS=2 for ketoprofen) of a cellulose $\alpha$-arylpropionate mixed chiral polymer, with a degree of substitution of 0.6 for $\alpha$-phenylpropionic acid and of 1.63 for ketoprofen, determined by elemental analysis, are obtained.

Analyses:

IR(KBr) $v_{max}$ (cm$^{-1}$): 3550–3450 (OH), 3000–2800 (—CH$_3$), 1760 and 1300 (ester C=O), 1680 (ketone C=O), 1600/1590/720/690 (aromatic C=C), 1450 ($\delta$as-CH$_3$), 1170 and 1090 (C=O/C—O).

$^1$H NMR (CDCl$_3$, 200 MHz) $\delta$ (ppm): 0.8–1.8 (m, $\alpha$-CH$_3$), 2–5 (m, cellulosic H+benzylic H), 6.6–8 (broad multiplet, aromatic H).

Elemental Analysis:

% calculated: C 73.63%, H 5.48% (DS=0.6 for $\alpha$-phenylpropionic acid and DS=2 for ketoprofen).

% obtained: C 71.79%, H 5.85% (DS=0.6 for $\alpha$-phenylpropionic acid and DS=1.63 for ketoprofen).

Optical rotation: [$\alpha$]$^{20}$=–73.0° ($\lambda$=436 nm, c=1 g/dm$^3$, CHCl$_3$).

Example 26

Synthesis of a Mixed Cellulose Ester of Ketoprofen and of α-Phenylpropionic Acid (with Intermediate Purification and Analyses)

❶Synthesis of a Cellulose Ketoprofenate of DS=1: See Example 17.

❷Synthesis of the Mixed Ester by Adding 4 Equivalents of α-Phenylpropionic Acid Chloride to the Preceding Phase:

The process is performed as in the second part of Example 25, but replacing the cellulose α-phenylpropionate of DS=0.6 with cellulose ketoprofenate of DS=1 (of Example 16) and the addition of ketoprofen chloride by adding 4 equivalents of α-phenylpropionic acid chloride; with 1.01 g of cellulose ketoprofenate chiral polymer of DS=1, 1.9 g (5 equivalents) of racemic α-phenylpropionic acid chloride, 30 ml of pyridine and heating at 105° C. for 48 h. 0.96 g (yield=57% on the basis of a polymer of DS=1 for ketoprofen and of DS=2 for α-phenylpropionic acid) of a cellulose α-arylpropionate mixed chiral polymer with a degree of substitution of 1 for ketoprofen and of 0.55 for α-phenylpropionic acid, determined by elemental analysis, is obtained.

Analyses:

IR(KBr) $v_{max}$ (cm$^{-1}$): 3500–3400 (OH), 3000–2800 (—CH$_3$), 1760 and 1300 (ester C=O), 1670 (ketone C=O), 1600/1500/730/710 (aromatic C=C), 1450 (δas-CH$_3$), 1170 and 1090 (C=O/C—O).

$^1$H NMR (CDCl$_3$, 200 MHz) δ (ppm): 0.7–1.8 (m, α-CH$_3$), 2.5–5 (m, cellulosic H+benzylic H), 6.8–7.8 (broad multiplet, aromatic H).

Elemental Analysis:

% calculated: C 72.52%, H 5.74% (DS=1 for ketoprofen and DS=2 for α-phenylpropionic acid).

% obtained: C 68.61%, H 6.01% (DS=1 for ketoprofen and DS=0.55 for α-phenylpropionic acid).

Optical rotation: $[\alpha]^{20}$=−80.0° (λ=436 nm, c=1 g/dm$^3$, CHCl$_3$).

Example 27

Synthesis of Cellulose Naproxenate from S(+) Naproxen (9 Eq.) in a Pyridine/Triethylamine/DMAP Mixture 0.5 g (3.09 mmol) of cellulose predried overnight under vacuum at 120° C., 25 ml of a pyridine/triethylamine mixture (2/1) predistilled and stored over KOH and 3 Å molecular sieves, respectively, and a catalytic amount of 4-dimethylaminopyridine (DMAP) are introduced into a 100 ml three-necked round-bottomed flask fitted with a condenser on which is mounted a calcium chloride guard tube and an addition funnel.

The cellulose is swollen in this mixture at 80° C. for half an hour. A solution of 6.9 g (9 eq.) of S(+) naproxen chloride dissolved in 50 ml of CH$_2$Cl$_2$ (dried over molecular sieves) is then added to the reaction medium at this temperature, over about one hour. The dichloromethane is stripped off with a stream of nitrogen. The mixture is then refluxed at 120° C. for 16 h.

After cooling, the mixture is poured into 150 ml of MeOH. A beige-colored precipitate forms immediately. This precipitate is filtered off and washed in 150 ml of MeOH with ultrasound for 15 min. The precipitate is again filtered off on a Büchner funnel and dried: 1 g (yield=41% on the basis of a trisubstitution) of crude cellulose ester with a DS=2.7 determined by elemental analysis is recovered. The solid is dissolved in 200 ml of CH$_2$Cl$_2$; the mixture obtained is filtered through cotton wool to give a clear solution. The CH$_2$Cl$_2$ solution is concentrated and then added dropwise to 50 ml of methanol. The precipitate obtained in powder form is filtered through a membrane (0.45 micron) and then washed by ultrasound with 20 ml of an iPrOH/hexane mixture (10/90). The resulting product is filtered off again on a membrane and, after drying at 60° C. in a vacuum oven, 650 mg (yield=26.4%) of cellulose naproxenate with a degree of substitution DS=2.8 determined by elemental analysis are obtained.

Analyses:

IR(KBr) $v_{max}$ (cm$^{-1}$): 2937 (δ CH), 1742 (δ C=O), 1607 and 1510 ($δ_{as}$ and $δ_s$ C=C), 1268 ($δ_{as}$ CH$_3$—O-aryl), 1070–1153 (δ (C=O)—O).

$^1$H NMR (CDCl$_3$, 200 MHz) δ (ppm): 0.4–1.8 (m, α-CH$_3$) 2.7–5.1 (m, O—CH$_3$+cellulosic H+benzylic H), 6.4–7.8 (m, aromatic H).

Elemental Analysis:

% calculated: C 72.18%, H 5.76% (for a trisubstitution).

% obtained: C 71.48%, H 5.57% for DS=2.7.

% obtained: C 71.81%, H 5.78% for DS=2.8.

Optical rotation: $[\alpha]^{20}$=−37.0° (λ=436 nm, c=1 g/dm$^3$, CHCl$_3$).

The distribution of the R and S attached acyl units is respectively 43% and 57% (distribution determined by hydrolysis, cf. Example 56).

Example 27A

Comparative Synthesis of Cellulose Naproxenate from S(+) Naproxen (1.5 Equivalents) in a Pyridine/Triethylamine/DMAP Mixture (Reaction for 24H at 120° C.)

The process is performed as in Example 27, but in the presence of 1.5 equivalents (instead of 9) of S(+) naproxen chloride and for 24 h. A cellulose naproxenate chiral polymer is thus obtained in a yield of 65% (on the basis of a monosubstitution) and with a DS=0.49 determined by elemental analysis.

The IR and NMR analyses are identical to those described in Example 18.

Elemental Analysis:

% calculated: C 64.17%, H 5.88% for a monosubstitution

% obtained: C 57.13%, H 5.73%

The distribution of the R and S attached ester units is respectively 48% and 52% (distribution determined by hydrolysis, cf. Example 56A).

Example 28

Synthesis of Cellulose Naproxenate from Racemic Naproxen (6 Eq.) in a Pyridine/Triethylamine/DMAP Mixture Working under the same conditions as with S(+) naproxen chloride (Example 27), 1.0 g (6.18 mmol) of cellulose is reacted this time with 9.32 g (6 eq.) of S,R-naproxen chloride dissolved in 40 ml.

After the same work-up, 1 g (yield=50% on the basis of a trisubstitution) of crude cellulose ester with a DS=2.6 determined by elemental analysis is obtained.

Analyses:

The IR and NMR spectra are identical to those obtained with S(+) naproxen chloride.

Elemental Analysis:
% calculated: C 72.18%, H 5.76% for a trisubstitution.
% obtained: C 71.43%, H 5.80%.

Optical rotation: $[\alpha]^{20}$=−30.0° ($\lambda$=436 nm, c=1 g/dm$^3$, CHCl$_3$).

The distribution of the R and S attached acyl units is respectively 44% and 56% (distribution determined by hydrolysis, cf. Example 57).

Example 28A

Comparative Synthesis of Cellulose Naproxenate from Racemic Naproxen (1.5 Equivalents) in a Pyridine/Triethylamine/DMAP Mixture (Reaction for 24H at 120° C.)

The process is performed as in Example 28, but in the presence of 1.5 equivalents (instead of 6) of racemic naproxen chloride. A cellulose naproxenate chiral polymer is thus obtained in a yield of 69% (on the basis of a monosubstitution) and with a DS=0.49 determined by elemental analysis. The IR and NMR analyses are identical to those described in Example 27A.

Elemental Analysis:
% calculated: C 64.17%, H 5.88% (for a monosubstitution).
% obtained: C 58.19%, H 5.78%.

The distribution of the R and S attached ester units is respectively 44% and 56% (distribution determined by hydrolysis, cf. Example 57A).

Example 29

Synthesis of Cellulose Naproxenate from Racemic Naproxen (2.1 Eq.) in a Pyridine/DMAP Mixture The reaction is carried out under the same conditions as in Example 27, but this time without triethylamine, in 30 ml of pyridine with a catalytic amount of DMAP.

1.0 g (6.18 mmol) of cellulose is reacted with 3.22 g (2.1 eq.) of S,R-naproxen chloride dissolved in 20 ml. The mixture is maintained at 100° C. for 48 h.

After the usual work-up, 2.85 g of cellulose ester with a DS=1.7 (yield=89% on the basis of a disubstitution) determined by elemental analysis are recovered.

Analyses:
IR(KBr) $v_{max}$ (cm$^{-1}$): 3437 ($\delta$ O—H), 2937 ($\delta$ C—H), 1742 ($\delta$ C=—O), 1607 and 1506 ($\delta_{as}$ and $\delta_s$ C=C), 1268 ($\delta_{as}$ CH$_3$—O-aryl), 1153–1070 ($\delta$ (C=O)—O).

$^1$H NMR (d$_5$-pyridine, 200 MHz) $\delta$ (ppm): 1.2–2.4 (m, $\alpha$-CH$_3$), 3.3–4.4 (m, O—CH$_3$+cellulosic H+benzylic H), 4.8–5.4 (m, cellulosic H); 6.5–8.5 (m, aromatic H).

Elemental Analysis:
% calculated: C 69.62%, H 5.63% for a disubstitution.
% obtained: C 68.41%, H 5.43%.

The optical rotation was not measured due to the poor solubility of the polymer in CHCl$_3$.

The distribution of the R and S attached acyl units is 60% and 40% respectively (distribution determined by hydrolysis, cf. Example 58).

Example 29A

Comparative Synthesis of Cellulose Naproxenate from Racemic Naproxen (7 Equivalents) in a Pyridine/DMAP Mixture (Reaction for 24H at 120° C.)

The process is performed as in Example 29, but in the presence of 7 equivalents (instead of 2.1) of racemic naproxen chloride. A cellulose naproxenate chiral polymer is thus obtained in a yield of 83% (on the basis of a trisubstitution) and with a DS=3.00 determined by elemental analysis. The IR and NMR analyses are identical to those described in Example 27.

Elemental Analysis:
% calculated: C 72.18%, H 5.76% (for a trisubstitution).
% obtained: C 72.18%, H 5.67%.

The distribution of the R and S attached ester units is 57% and 43% respectively (distribution determined by hydrolysis, cf. Example 58A).

Example 30

Synthesis of Cellulose Naproxenate from Racemic Naproxen (1.5 Eq.) in a Pyridine/DMAP Mixture Under the conditions described for the addition of racemic naproxen chloride (2.1 eq.) to cellulose (Example 29), 0.75 g (4.63 mmol) of cellulose is reacted with 1.72 g (1.5 eq.) of S,R-naproxen chloride.

After the usual work-up, 1.59 g of cellulose ester of DS$_{average}$=0.71 (yield=92% on the basis of a monosubstitution) determined by elemental analysis are recovered.

Analyses:
IR(KBr) $v_{max}$ (cm$^{-1}$): 3344 ($\delta$ O—H), 2937 and 2904 ($\delta$ C—H), 1740 ($\delta$ C=O), 1607 and 1506 ($\delta_{as}$ and $\delta_s$ C=C), 1266 ($\delta_{as}$ CH$_3$—O-aryl), 1162–1060 ($\delta$ (C=O)—O).

$^1$H NMR (d$_5$-pyridine, 200 MHz) $\delta$ (ppm): 1.2–2.0 (m, $\alpha$-CH$_3$), 3.3–4.4 (m, O—CH$_3$+cellulosic H+benzylic H), 4.9–5.7 (m, cellulosic H); 6.9–8.3 (m, aromatic H).

Elemental Analysis:
% calculated: C 64.17%, H 5.88% for a monosubstitution
% obtained: C 61.82%, H 5.48% for a DS=0.77
% obtained: C 60.30%, H 5.30% for a DS=0.65

The optical rotation was not measured due to the poor solubility of the polymer in CHCl$_3$.

The distribution of the R and S attached acyl units is 55% and 45% respectively (distribution determined by hydrolysis, cf. Example 59).

Example 31

Synthesis of Cellulose Naproxenate from S(+) Naproxen (2.1 Eq.) in a Pyridine/DMAP Mixture Under the conditions described in Example 29, 0.9 g (5.6 mmol) of cellulose is reacted with 2.82 g (11.4 mmol, 2.1 eq.) of S(+) naproxen chloride dissolved in CH$_2$Cl$_2$ at 40° C. The reaction is refluxed at 90° C. for 48 h.

After the usual work-up, 1.87 g (yield=57% on the basis of a disubstitution) of cellulose ester of DS=1.5 determined by elemental analysis are recovered.

Analyses:
The IR spectrum is identical to that obtained with the S,R-naproxen chloride of Example 29.

$^1$H NMR (d$_5$-pyridine, 200 MHz) δ (ppm): 1.2–2.0 (m, α-CH$_3$), 3.3–4.6 (m, O—CH$_3$+cellulosic H+benzylic H), 4.8–5.7 (m, cellulosic H); 6.8–8.3 (m, aromatic H).

Elemental Analysis:
% calculated: C 69.62%, H 5.63% for a disubstitution,
% obtained: C 67.72%, H 6.04%.

The optical rotation was not measured due to the poor solubility of the polymer in CHCl$_3$.

The distribution of the R and S attached acyl units is 53% and 47% respectively (distribution determined by hydrolysis, cf. Example 60).

Example 32

Synthesis of Cellulose Naproxenate from S(+) Naproxen (1 Eq.) in a Pyridine/DMAP Mixture Under the conditions described in Example 30, 1 g (6.2 mmol) of cellulose is reacted with 1.53 g (6.2 mmol, 1 eq.) of S(+) naproxen chloride.

After the usual work-up, 1.75 g (yield=76% on the basis of a monosubstitution) of cellulose ester of DS=0.6 determined by elemental analysis are recovered.

Analyses:

The IR and NMR spectra are identical to those obtained with the S,R-naproxen chloride of Example 30.

Elemental Analysis:
% calculated: C 64.17%, H 5.88% for a monosubstitution,
% obtained: C 59.43%, H 6.10%.

The optical rotation was not measured due to the poor solubility of the polymer in CHCl$_3$.

The distribution of the R and S attached acyl units is 53% and 47% respectively (distribution determined by hydrolysis, cf. Example 61).

Example 32A

Comparative Synthesis of Cellulose Naproxenate from S(+) Naproxen (7 Equivalents) in a Pyridine/DMAP Mixture (Reaction for 24H at 120° C.)

The process is performed as in Example 32, but in the presence of 7 equivalents (instead of 1) of S(+) naproxen chloride and for 24 h. A cellulose naproxenate chiral polymer is thus obtained in a yield of 82% (on the basis of a trisubstitution) and with a DS=2.80 determined by elemental analysis. The IR and NMR analyses are identical to those described in Example 27.

Elemental Analysis:
% calculated: C 72.18%, H 5.76% for a trisubstitution
% obtained: C 71.84%, H 5.75%

The distribution of the R and S attached ester units is 55% and 45% respectively (distribution determined by hydrolysis, cf. Example 61A).

Example 33

Synthesis of Amylose Naproxenate from S(+) Naproxen (6.2 Eq.) in a Pyridine/Triethylamine/DMAP Mixture Under the conditions described in Example 27, 0.2 g (1.3 mmol) of amylose is reacted with 2.0 g (8.0 mmol, 1 eq.) of S(+) naproxen chloride.

After the usual work-up, 170 mg (yield=16% on the basis of a trisubstitution) of amylose ester of DS=2.3 determined by elemental analysis are recovered.

Analyses:
IR(KBr) v$_{max}$ (cm$^{-1}$): 3442 (δ O—H), 2937 (δ C—H), 1737 (δ C=O), 1606 and 1506 (δ$_{as}$ and δ$_s$ C=C), 1266 (δ$_{as}$ CH$_3$—O-aryl), 1162–1032 (δ (C=O)—O).

$^1$H NMR (CDCl$_3$, 200 MHz) δ (ppm): 0.3–2.0 (m, α-CH$_3$), 2.5–5.7 (m, O—CH$_3$+cellulosic H+benzylic H), 6.4–8.0 (m, aromatic H).

Elemental Analysis:
% calculated: C 72.18%, H 5.76% for a monosubstitution.
% obtained: C 70.32%, H 6.49%.

Optical rotation: [α]$^{20}$=+29.0° (λ=436 nm, c=1 g/dm$^3$, CHCl$_3$).

Example 34

Synthesis of β-Cyclodextrin Naproxenate from Racemic Naproxen (6 Eq.) in Pyridine 0.5 g (3.09 mmol) of β-cyclodextrin predried overnight under vacuum at 120° C., and 15 ml of pyridine predistilled and dried over KOH are placed in a 100 ml three-necked round-bottomed flask fitted with a condenser on which is mounted a calcium chloride guard tube, and an addition funnel.

The mixture is brought to 80° C. and then cooled. A solution of 5.0 g (6 eq.) of racemic naproxen chloride dissolved in 15 ml of CH$_2$Cl$_2$ (dried over molecular sieves) is then added to the reaction medium at room temperature over 5 min. The mixture is then refluxed gently at 40° C. for 16 h. Next, the dichloromethane is stripped off with a stream of nitrogen and the reaction mixture is refluxed in pyridine for 3 h.

After cooling, the mixture is diluted with 50 ml of CH$_2$Cl$_2$ and washed with saturated sodium bicarbonate solution, then with 3M HCl solution and finally with water. The organic phase is dried over MgSO$_4$ and concentrated. The solution obtained is poured into 30 ml of MeOH. A white precipitate of β-cyclodextrin ester forms immediately. This ester is filtered off and dried and then dissolved in 10 ml of CH$_2$Cl$_2$. The solution in CH$_2$Cl$_2$ is again added dropwise to 25 ml of MeOH with stirring to give a precipitate washed of its impurities. The dichloromethane is then evaporated off and the precipitate, once filtered off and dried under vacuum at 25° C. for 4 h, is obtained in the form of a very fine powder: 2.20 g (yield=89% on the basis of a trisubstitution), DS=2.81 determined by elemental analysis.

Analyses:
IR(KBr) v$_{max}$ (cm$^{-1}$): 1760 (δ C=O), 1510 (δ$_{as}$ CH$_3$) 1170 and 1090 (δ (CO)—O).

$^1$H NMR (CDCl$_3$, 200 MHz) δ (ppm): 0.8–1.7 (m, α-CH$_3$), 2.9–5.1 (m, O—CH$_3$+cyclodextrin H+benzylic H), 6.8–8.0 (m, aromatic H).

Elemental Analysis:
% calculated: C 72.18%, H 5.76% for a trisubstitution
% obtained: C 71.81%, H 6.02%.

Optical rotation: [α]$^{20}$=258.2° (λ=436 nm, c=2.8 g/dm$^3$, CHCl$_3$).

[α]$^{20}$=119.6° (λ=589 nm, c=2.8 g/dm$^3$, CHCl$_3$)

The distribution of the R and S attached ester units is 50% and 50% respectively (distribution determined by hydrolysis, cf. Example 62).

C—Enrichment by Hydrolysis of the Phases

Example 35

Hydrolysis of Cellulose α-Phenylpropionate
(DS=2.94, Example 1)

0.247 g (0.45 mmol) of cellulose α-phenylpropionate is placed in 70 ml of tetrahydrofuran (THF) at room temperature. The mixture is stirred in order to dissolve the phase, followed by addition of 10 ml of distilled water and 0.17 g (0.4 mmol) of LiOH monohydrate (M=42 g). This mixture is stirred at room temperature for 24 h.

10 ml of water are added and the THF is evaporated off under reduced pressure. The mixture is cooled to 0° C. and 2 ml of 2M sodium hydroxide solution are added. The resulting mixture is stirred for 30 min and is then filtered to recover the residual hydrolyzed phase. The aqueous phase is washed twice with 10 ml of dichloromethane to remove the organic impurities. After acidification with aqueous 3M hydrochloric acid solution, extraction with 3 times 20 ml of ether, drying over $MGSO_4$ and concentrating to dryness under reduced pressure, 0.198 g (1.32 mmol) of α-phenylpropionic acid is obtained.

The hydrolysis yield is quantitative and the acid recovered is analyzed by NMR.

$^1$H NMR ($CDCl_3$, 200 MHz) δ (ppm): 1.55 (d, 3H, α-$CH_3$), 3.75 (q, 1H, benzylic H), 7.2–7.4 (m, 5H, aromatic H), 10.2–10.9 (m, 1H, acid H).

The hydrolyzed phase recovered is analyzed by solid IR (KBr): its spectrum is identical to that of the starting cellulose.

The enantiomeric composition of this acid was determined by chiral HPLC on a Chiralcel OD-H column (250*4 mm, 5 μm, Daicel Japan) with the following analysis conditions: hexane/iPrOH/$CF_3COOH$: 98/1.95/0.05, 0.75 ml/min, λ=230 nm. 2 peaks are obtained at Rt=12.27 min (62%) and Rt=14.55 min (38%).

The literature indicates that the 1st peak corresponds to the R(−) form.

Example 35A

Hydrolysis of Cellulose α-Phenylpropionate
(DS=2.97, Example 1A)

The process is performed as in Example 35. The hydrolysis yield is quantitative and the structure of the acid recovered is confirmed by NMR. The hydrolyzed phase recovered is analyzed by solid IR (KBr): its spectrum is identical to that of the starting cellulose. The enantiomeric composition of this acid was determined by chiral HPLC under the same conditions as in Example 35. The percentages of the two enantiomers R(−) and S(+) are 68% and 32% respectively.

Example 35B

Hydrolysis of Cellulose α-Phenylpropionate
(DS=2.96, Example 1B)

The process is performed as in Example 35. The hydrolysis yield is quantitative and the structure of the acid recovered is confirmed by NMR. The hydrolyzed phase recovered is analyzed by solid IR (KBr): its spectrum is identical to that of the starting cellulose. The enantiomeric composition of this acid was determined by chiral HPLC under the same conditions as in Example 35. The percentages of the two enantiomers R(−) and S(+) are 47% and 53% respectively.

Example 35C

Hydrolysis of Cellulose α-Phenylpropionate
(DS=2.00, Example 1C)

The process is performed as in Example 35. The hydrolysis yield is quantitative and the structure of the acid recovered is confirmed by NMR. The hydrolyzed phase recovered is analyzed by solid IR (KBr): its spectrum is identical to that of the starting cellulose. The enantiomeric composition of this acid was determined by chiral HPLC under the same conditions as in Example 35. The percentages of the two enantiomers R(−) and S(+) are 46% and 54% respectively.

Example 35D

Hydrolysis of Cellulose α-Phenylpropionate
(DS=1.87, Example 1D)

The process is performed as in Example 35. The hydrolysis yield is quantitative and the structure of the acid recovered is confirmed by NMR. The hydrolyzed phase recovered is analyzed by solid IR (KBr): its spectrum is identical to that of the starting cellulose. The enantiomeric composition of this acid was determined by chiral HPLC under the same conditions as in Example 35. The percentages of the two enantiomers R(−) and S(+) are 43% and 57% respectively.

Example 35E

Hydrolysis of Cellulose α-Phenylpropionate
(DS=1.13, Example 1E)

The process is performed as in Example 35. The hydrolysis yield is quantitative and the structure of the acid recovered is confirmed by NMR. The hydrolyzed phase recovered is analyzed by solid IR (KBr): its spectrum is identical to that of the starting cellulose. The enantiomeric composition of this acid was determined by chiral HPLC under same conditions as in Example 35. The percentages of the two enantiomers R(−) and S(+) are 54% and 46% respectively.

Example 35F

Hydrolysis of Amylopectin α-Phenylpropionate
(DS=2.92, Example 1F)

The process is performed as in Example 35. The hydrolysis yield is quantitative and the structure of the acid recovered is confirmed by NMR. The hydrolyzed phase recovered is analyzed by solid IR (KBr): its spectrum is identical to that of the starting glucidex. The enantiomeric composition of this acid was determined by chiral HPLC under the same conditions as in Example 35. The percentages of the two enantiomers R(−) and S(+) are 49% and 51% respectively.

Example 36

Hydrolysis of Cellulose α-Phenylpropionate
(DS=2.5, Example 3)

The process is performed as in Example 35, but with stirring for 72 h at room temperature instead of 24 h; with 0.098 g of phase, 0.091 g of LiOH monohydrate, 60 ml of THF. 0.081 g (0.54 mmol) of α-phenylpropionic acid is thus obtained.

The hydrolysis yield is quantitative and the acid recovered is analyzed by NMR.

$^1$H NMR (CDCl$_3$, 200 MHz) β (ppm): 1.55 (d, 3H, α-CH$_3$), 3.75 (q, 1H, benzylic H), 7.2–7.4 (m, 5H, aromatic H) 9.8–11.2 (m, 1H, acid H).

The hydrolyzed phase recovered is analyzed by solid IR (KBr): its spectrum is identical to that of the starting cellulose.

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 99/0.95/0.05, 1 ml/min, λ=230 nm. 2 peaks are obtained at Rt=18.35 min (58.4%) and Rt=23.06 min (41.6%).

The literature indicates that the 1st peak corresponds to the R(−) form.

The predominance of the (−) enantiomer is confirmed by the optical rotation of the mixture thus obtained.

Optical rotation: [α]$^{20}$=9.4° (λ=589 nm, c=16 g/dm$^3$, CHCl$_3$).

Example 37

Hydrolysis of Cellulose α-Phenylpropionate
(DS=2.5, Example 4)

The process is performed as in Example 35, but with a stirring time of 72 h instead of 24 h; with 0.12 g of phase, 0.114 g of LiOH monohydrate, 60 ml of THF. 0.085 g (0.57 mmol) of α-phenylpropionic acid is thus obtained.

The hydrolysis yield is quantitative and the acid recovered is analyzed by NMR:

$^1$H NMR (CDCl$_3$, 200 MHz) δ (ppm): 1.55 (d, 3H, α-CH$_3$), 3.75 (q, 1H, benzylic H), 7.27–7.32 (m, 5H, aromatic H), 11–11.7 (m, 1H, acid H).

The hydrolyzed phase recovered is analyzed by solid IR (KBr): its spectrum is identical to that of the starting cellulose.

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 99/0.95/0.05, 1 ml/min, λ=230 nm. 2 peaks are obtained at Rt=18.10 min (58.3%) and Rt=22.47 min (41.7%).

The literature indicates that the 1st peak corresponds to the R(−) form.

The predominance of the (−) enantiomer is confirmed by the optical rotation of the mixture thus obtained.

Optical rotation: [α]$^{20}$=−9.0° (λ=589 nm, c=14 g/dm$^3$, CHCl$_3$).

Example 38

Hydrolysis of Cellulose α-Phenylpropionate
(DS=1.99, Example 6)

The process is performed as in Example 35, with 0.21 g of phase, 0.165 g of LiOH monohydrate, 60 ml of THF and hydrolysis for 24 h. 0.04 g (0.27 mmol) of α-phenylpropionic acid is thus obtained.

The hydrolysis yield is 27% and the acid recovered is analyzed by NMR.

$^1$H NMR (CDCl$_3$, 200 MHz) δ (ppm): 1.55 (d, 3H, α-CH$_3$) 3.75 (q, 1H, benzylic H), 7.27–7.32 (m, 5H, aromatic H), 11–11.7 (m, 1H, acid H).

The hydrolyzed phase recovered is analyzed by solid IR (KBr): its spectrum is identical to that of the starting cellulose.

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 98/1.95/0.05, 0.75 ml/min, λ=230 nm. 2 peaks are obtained at Rt=12.31 min (59.6%) and Rt=14.59 min (40.4%).

The literature indicates that the 1st peak corresponds to the R(−) form.

Example 39

Hydrolysis of Cellulose α-Phenylpropionate
(DS=0.91, Example 7)

The process is performed as in Example 35, with 0.103 g of phase, 0.13 g of LiOH monohydrate, 50 ml of THF and hydrolysis for 72 h. 0.056 g (0.37 mmol) of α-phenylpropionic acid is thus obtained.

The hydrolysis yield is quantitative and the acid recovered is analyzed by NMR.

$^1$H NMR (CDCl$_3$, 200 MHz) δ (ppm): 1.55 (d, 3H, α-CH$_3$), 3.75 (q, 1H, benzylic H), 7.27–7.32 (m, 5H, aromatic H), 11–11.7 (m, 1H, acid H).

The cellulose recovered after hydrolysis is analyzed by solid IR (KBr): its spectrum is identical to that of the starting cellulose.

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 99/0.95/0.05, 1 ml/min, λ=230 nm. 2 peaks are obtained at Rt=22.38 min (58%) and Rt=28.24 min (42%).

The literature indicates that the 1st peak corresponds to the R(−) form.

The predominance of the (−) enantiomer is confirmed by the optical rotation of the mixture thus obtained.

Optical Rotation:
[α]$^{20}$=−10.8° (λ=589 nm, c=3.6 g/dm$^3$, CHCl$_3$).
[α]$^{20}$=−22.5° (λ=436 nm, c=3.6 g/dm$^3$, CHCl$_3$).

Example 40

Hydrolysis of Amylose α-Phenylpropionate
(DS=3.0, Example 8)

The process is performed as in Example 35, the reaction mixture being stirred at room temperature for 72 h instead of 24 h; with 0.103 g of phase, 0.082 g of LiOH monohydrate, 60 ml of THF. 0.077 g (0.51 mmol) of α-phenylpropionic acid is thus obtained.

The hydrolysis yield is quantitative and the acid recovered is analyzed by NMR.

$^1$H NMR (CDCl$_3$, 200 MHz) δ (ppm): 1.52 (d, 3H, α-CH$_3$), 3.7 (q, 1H, benzylic H), 7.27–7.32 (m, 5H, aromatic H), 11.1–11.5 (m, 1H, acid H).

The amylose remained in solution and could not be recovered by filtration.

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 99/0.95/0.05, 1 ml/min, λ=230 nm. 2 peaks are obtained at Rt=18.23 min (53%) and Rt=22.79 min (47%).

The literature indicates that the 1st peak corresponds to the R(−) form.

The predominance of the (−) enantiomer is confirmed by the optical rotation of the mixture thus obtained.

Optical rotation: $[α]^{20}$=−4.0° (λ=589 nm, c=19 g/dm$^3$, CHCl$_3$).

Example 41

Hydrolysis of Cellulose
α-(p-Chlorophenyl)Propionate (DS=3, Example 10)

Working as in Example 35, with 0.187 g of phase, 0.18 g of LiOH monohydrate, 60 ml of THF and hydrolysis for 24 h, 0.16 g (0.87 mmol) of α-(p-chlorophenyl)propionic acid is obtained.

The hydrolysis yield is quantitative and the acid recovered is analyzed by NMR.

$^1$H NMR (CDCl$_3$, 200 MHz) δ (ppm): 1.48 (d, 3H, α-CH$_3$), 3.7 (q, 1H, benzylic H), 7.14–7.38 (m, 4H, aromatic H), 10.8–11.2 (m, 1H, acid H).

The hydrolyzed phase recovered is analyzed by solid IR (KBr): its spectrum is identical to that of the starting cellulose.

The enantiomeric composition of this acid was determined by chiral HPLC on an (R—R)-Whelk-0-1 column (Lichrocart 250*4 mm, 5 μm, Merck) with the following analysis conditions: hexane/iPrOH/CH$_3$COOH: 98/1.5/0.5, 0.8 ml/min, λ=230 nm. 2 peaks are obtained at Rt=6.8 min (43.7%) and Rt=8.5 min (56.3%).

The sign of the optical rotation indicates an enrichment in (−) enantiomer which thus corresponds to the 2nd peak.

Optical rotation: $[α]^{20}$=−8.0° (λ=589 nm, c=14 g/dm$^3$, CHCl$_3$).

Example 42

Deracemization and then Hydrolysis of Cellulose
α-(p-Chlorophenyl)Propionate (DS=3, Example 10)
Using Lithium Diisopropylamide 0.3 g (0.45 mmol) of cellulose α-(p-chlorophenyl)propionate is introduced into 50 ml of tetrahydrofuran (THF) at room temperature. The mixture is stirred in order to dissolve the phase and is cooled to −10° C. 1.6 ml (3.3 mmol) of a 2M solution of LDA are added dropwise, with stirring and still at −10° C. The mixture is stirred at −10° C. for 2 h, followed by addition of 0.5 ml (30 mmol) of distilled water. The mixture is warmed to room temperature and stirred for a further 12 h at room temperature. 20 ml of water are added and the THF is evaporated off under reduced pressure. The mixture is cooled to 0° C. and 1 ml of 2M sodium hydroxide solution is added. This mixture is stirred for 30 min and then filtered to recover the residual hydrolyzed phase.

The aqueous phase is washed twice with 10 ml of dichloromethane to remove the organic impurities. After acidifying with aqueous 3M hydrochloric acid solution, extracting with 3 times 20 ml of ether, drying over MgSO$_4$ and concentrating to dryness under reduced pressure, 0.241 g (1.31 mmol) of α-(p-chlorophenyl)propionic acid is obtained.

The hydrolysis yield is quantitative and the acid recovered is analyzed by NMR.

$^1$H NMR (CDCl$_3$, 200 MHz) δ (ppm): 1.5 (d, 3H, α-CH$_3$), 3.7 (q, 1H, benzylic H), 7.25–7.3 (m, 4H, aromatic H), 10–11.5 (m, 1H, acid H).

The enantiomeric composition of this acid was determined by chiral HPLC on an (R—R)-Whelk-0-1 column (Lichrocart 250*4 mm, 5 μm, Merck) with the following analysis conditions: hexane/iPrOH/CH$_3$COOH: 98/1.5/0.5, 0.8 ml/min, λ=230 nm. 2 peaks are obtained at Rt=7.92 min (50.6%) and Rt=8.9 min (49.4%).

The sign of the optical rotation indicated an enrichment in (+) enantiomer which thus corresponds to the 1st peak.

Optical rotation: $[α]^{20}$=0.5° (λ=589 nm, c=2 g/dm$^3$, CHCl$_3$).

Example 43

Deracemization and then Hydrolysis of Cellulose
α-(p-Chlorophenyl)Propionate (DS=3, Example 10)
Using Triethylamine 0.2 g (0.3 mmol) of cellulose α-(p-chlorophenyl)propionate and 1 g (0.01 mol) of triethylamine are introduced into 50 ml of dichloromethane at room temperature. The flask is sealed and placed in a bath thermostatically maintained at 30° C., for 14 days. The mixture is washed with 3M hydrochloric acid solution and then with water. The organic phase is dried over MgSO$_4$ and then evaporated to dryness under reduced pressure. The deracemized phase is recovered and hydrolyzed using a lithium hydroxide/water mixture, according to the above hydrolysis procedure. 0.161 g (0.9 mmol) of α-(p-chlorophenyl)propionic acid is recovered.

The hydrolysis yield is quantitative and the structure of the acid recovered is confirmed by $^1$H-NMR.

The enantiomeric composition of this acid was determined by chiral HPLC on an (R—R)-Whelk-0-1 column (Lichrocart 250*4 mm, 5 μm, Merck) with the following analysis conditions: hexane/iPrOH/CH$_3$COOH: 98/1.5/0.5, 0.8 ml/min, λ=230 nm. 2 peaks are obtained at Rt=7.68 min (49.7%) and Rt=8.57 min (50.3%).

Example 44

Hydrolysis of Amylose (p-Chlorophenyl)Propionate
(DS=3, Example 13)

The process is performed as in Example 35, with 0.109 g of phase, 0.074 g of LiOH monohydrate, 60 ml of THF and hydrolysis for 72 h. 0.1 g (0.54 mmol) of α-(p-chlorophenyl)propionic acid is thus obtained.

The hydrolysis yield is quantitative and the acid recovered is analyzed by NMR.

$^1$H NMR (CDCl$_3$, 200 MHz) δ (ppm): 1.48 (d, 3H, α-CH$_3$), 3.7 (q, 1H, benzylic H), 7.21–7.32 (m, 4H, aromatic H), 8.2–9.2 (m, 1H, acid H).

The amylose remained in solution and could not be recovered by filtration.

The enantiomeric composition of this acid was determined by chiral HPLC on an (R—R)-Whelk-0-1 column (Lichrocart 250*4 mm, 5 μm, Merck) with the following analysis conditions: hexane/iPrOH/CH$_3$COOH: 98/1.5/0.5, 1 ml/min, λ=230 nm. 2 peaks are obtained at Rt=6.28 min (47.7%) and Rt=7.24 min (52.3%).

The sign of the optical rotation indicates an enrichment in (−) enantiomer which thus corresponds to the 2nd peak.
Optical rotation: $[\alpha]^{20}=-2.0°$ ($\lambda=589$ nm, $c=19$ g/dm$^3$, CHCl$_3$).

Example 45

Hydrolysis of Cellulose Ketoprofenate (DS=2.35, Example 14)

The process is performed as in Example 35, with 0.113 g of phase, 0.071 g of LiOH monohydrate, 60 ml of THF and hydrolysis for 72 h. 0.078 g (0.31 mmol) of ketoprofen is thus obtained.

The hydrolysis yield is 83% and the acid recovered is analyzed by NMR.

$^1$H NMR (CDCl$_3$, 200 MHz) δ (ppm): 1.52 (d, 3H, α-CH$_3$), 3.8 (q, 1H, benzylic H), 7.23–7.8 (m, 9H, aromatic H), 10.2–10.6 (m, 1H, acid H).

The hydrolyzed phase recovered is analyzed by solid IR (KBr): its spectrum is identical to that of the starting cellulose, with a very weak C=O band at 1760 cm$^{-1}$ and 1680 cm$^{-1}$.

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 98/1.95/0.05, 1 ml/min, λ=230 nm. 2 peaks are obtained at Rt=29.22 min (58.3%) and Rt=31.84 min (41.7%).

The literature indicates that the 1st peak corresponds to the R(−) form.

The predominance of the (−) enantiomer is confirmed by the optical rotation of the mixture thus obtained.

Optical Rotation:
$[\alpha]^{20}=4.5°$ ($\lambda=589$ nm, $c=4.4$ g/dm$^3$, CHCl$_3$).
$[\alpha]^{20}=-9.3°$ ($\lambda=436$ nm, $c=4.4$ g/dm$^3$, CHCl$_3$).

Example 46

Hydrolysis of Cellulose Ketoprofenate (DS=2.9, Example 15)

Working as in Example 35, with 0.099 g of phase, 0.051 g of LiOH monohydrate, 50 ml of THF and hydrolysis for 48 h, 0.084 g (0.33 mmol) of ketoprofen is obtained.

The hydrolysis yield is 97% and the acid recovered is analyzed by NMR.

$^1$H NMR (CDCl$_3$, 200 MHz) δ (ppm): 1.52 (d, 3H, α-CH$_3$), 3.8 (q, 1H, benzylic H), 7.23–7.8 (m, 9H, aromatic H), 10.2–10.6 (m, 1H, acid H).

The hydrolyzed phase recovered is analyzed by solid IR (KBr): its spectrum, which is identical to that of the starting cellulose, shows a weak C=O band at 1760 cm$^{-1}$ and 1680 cm$^{-1}$.

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 99/0.95/0.05, 1 ml/min, λ=230 nm. 2 peaks are obtained at Rt=63.79 min (49.5%) and Rt=70.86 min (50.5%).

The literature indicates that the 2nd peak corresponds to the S(+) form.

The predominance of the (+) enantiomer is confirmed by the optical rotation of the mixture thus obtained.

Optical Rotation:
$[\alpha]^{20}=0.2°$ ($\lambda=589$ nm, $c=5.2$ g/dm$^3$, CHCl$_3$).
$[\alpha]^{20}=0.4°$ ($\lambda=436$ nm, $c=5.2$ g/dm$^3$, CHCl$_3$).

Example 47

Hydrolysis of Amylose Ketoprofenate (DS=2.42, Example 16)

Working as in Example 35, with 0.1063 g of phase, 0.068 g of LiOH monohydrate, 50 ml of THF and hydrolysis for 72 h, 0.085 g (0.34 mmol) of ketoprofen is obtained.

The hydrolysis yield is quantitative and the acid recovered is analyzed by NMR.

$^1$H NMR (CDCl$_3$, 200 MHz) δ (ppm): 1.54 (d, 3H, α-CH$_3$), 3.8 (q, 1H, benzylic H), 7.23–8 (m, 9H, aromatic H), 8.2–8.8 (m, 1H, acid H).

The amylose remained in solution and could not be recovered by filtration.

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 99/0.95/0.05, 1 ml/min, λ=230 nm. 2 peaks are obtained at Rt=62.46 min (50.7%) and Rt=69.12 min (49.3%).

The literature indicates that the 1st peak corresponds to the R(−) form.

The predominance of the (−) enantiomer is confirmed by the optical rotation of the mixture thus obtained.

Optical Rotation:
$[\alpha]^{20}=-0.9°$ ($\lambda=589$ nm, $c=3.4$ g/dm$^3$, CHCl$_3$).
$[\alpha]^{20}=-0.9°$ ($\lambda=436$ nm, $c=3.4$ g/dm$^3$, CHCl$_3$).

Example 48

Hydrolysis of Cellulose Monoketoprofenate (DS=1, Example 17)

Working as in Example 35, with 0.202 g of phase, 0.13 g of LiOH monohydrate, 50 ml of THF and hydrolysis for 24 h, 0.169 g (0.67 mmol) of ketoprofen is obtained.

The hydrolysis yield is 71% and the acid recovered is analyzed by NMR.

$^1$H NMR (CDCl$_3$, 200 MHz) δ (ppm): 1.5 (d, 3H, α-CH$_3$), 3.7 (q, 1H, benzylic H), 7.23–8 (m, 9H, aromatic H), 9.2–10 (m, 1H, acid H).

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 98/1.95/0.05, 0.8 ml/min, λ=230 nm. 2 peaks are obtained at Rt=30.43 min (55.3%) and Rt=32.75 min (44.7%).

The literature indicates that the 1st peak corresponds to the R(−) form.

The predominance of the (−) enantiomer is confirmed by the optical rotation of the mixture thus obtained.

Optical rotation: $[\alpha]^{20}=-3.3°$ ($\lambda=436$ nm, $c=2$ g/dm$^3$, CHCl$_3$).

Example 49

Hydrolysis of Cellulose Ibuprofenate (DS=2.73, Example 18)

Working as in Example 35, with 0.102 g of phase, 0.61 g of LiOH monohydrate, 50 ml of THF and hydrolysis for 72 h, 0.035 g (0.17 mmol) of ketoprofen is obtained.

The hydrolysis yield is 50% and the acid recovered is analyzed by NMR.

$^1$H NMR (CDCl$_3$, 200 MHz) δ (ppm): 1.2 (d, 6H, (CH$_3$)$_2$—CH), 1.4 (d, 3H, α-CH$_3$), 1.8 (sept, 1H, (CH$_3$)$_2$—CH), 2.4 (d, 2H, CH$_2$—CH$_3$), 3.7 (q, 1H, benzylic H), 7–7.25 (m, 4H, aromatic H), 9–10 (m, 1H, acid H).

The hydrolyzed phase recovered is analyzed by solid IR (KBr): the presence of a strong OH band but also of the C=O band at 1760 cm$^{-1}$ are observed, which confirms that the hydrolysis was only partial.

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 99/0.95/0.05, 1 ml/min, λ=230 nm. 2 peaks are obtained at Rt=11.66 min (63.3%) and Rt=13.99 min (36.7%).

The literature indicates that the 1st peak corresponds to the R(−) form.

The predominance of the (−) enantiomer is confirmed by the optical rotation of the mixture thus obtained.

Optical rotation: $[\alpha]^{20}$=−10.1° (λ=589 nm, c=7 g/dm$^3$, CHCl$_3$).

Example 49A

Hydrolysis of Cellulose Ibuprofenate (DS=2.77, Example 18A)

The process is performed as in Example 49, but for 10 days. The hydrolysis yield is quantitative and the structure of the acid recovered is confirmed by NMR. The hydrolyzed phase recovered is analyzed by solid IR (KBr): its spectrum is identical to that of the starting cellulose. The enantiomeric composition of this acid was determined by chiral HPLC under the same conditions as in Example 49. The percentages of the two enantiomers R(−) and S(+) are 48% and 52% respectively.

Example 50

Hydrolysis of Cellulose α-(3,5-Dimethylphenyl)Propionate (DS=1.74, Example 20)

Working as in Example 35, with 0.148 g of phase, 0.101 g of LiOH monohydrate, 60 ml of THF and hydrolysis for 72 h, 0.117 g (0.66 mmol) of 3,5-dimethylphenylpropionic acid is obtained.

The hydrolysis yield is quantitative and the acid recovered is analyzed by NMR.

$^1$H NMR (CDCl$_3$, 200 MHz) δ (ppm): 1.48 (d, 3H, α-CH$_3$), 2.29 (s, 6H, CH$_3$—Ar), 3.67 (q, 1H, benzylic H), 6.92 (s, 3H, aromatic H), 9.5–11 (m, 1H, acid H).

The hydrolyzed phase recovered is analyzed by solid IR (KBr): its spectrum is identical to that of the starting cellulose.

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 99/0.95/0.05, 1 ml/min, λ=230 nm. 2 peaks are obtained at Rt=16.79 min (58%) and Rt=28.27 min (42%).

The sign of the optical rotation indicates an enrichment in (−) enantiomer which is thus the 1st peak.

Optical Rotation:

$[\alpha]^{20}$=−8.0° (λ=589 nm, c=4 g/dm$^3$, CHCl$_3$).

$[\alpha]^{20}$=−17.0° (λ=436 nm, c=4 g/dm$^3$, CHCl$_3$)

Example 51

Hydrolysis of Cellulose α-(3,5-Dimethylphenyl)Propionate (DS=3, Example 21)

Working as in Example 35, with 0.124 g of phase, 0.84 g of LiOH monohydrate, 60 ml of THF and hydrolysis for 72 h, 0.091 g (0.51 mmol) of 3,5-dimethylphenylpropionic acid is obtained.

The hydrolysis yield is 90% and the acid recovered is analyzed by NMR.

$^1$H NMR (CDCl$_3$, 200 MHz) δ (ppm): 1.5 (d, 3H, α-CH$_3$), 2.29 (s, 6H, CH$_3$—Ar), 3.7 (q, 1H, benzylic H), 6.92 (s, 3H, aromatic H), 9.5–11 (m, 1H, acid H).

The hydrolyzed phase recovered is analyzed by solid IR (KBr): its spectrum is identical to that of the starting cellulose with a very weak C=O band at 1760 cm$^{-1}$.

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 98/1.95/0.05, 0.8 ml/min, λ=230 nm. 2 peaks are obtained at Rt=10.11 min (63%) and Rt=13.84 min (37%).

The sign of the optical rotation indicates an enrichment in (−) enantiomer which thus corresponds to the 1st peak.

Optical Rotation:

$[\alpha]^{20}$=−15.7° (λ=589 nm, c=22 g/dm$^3$, CHCl$_3$).

$[\alpha]^{20}$=−33.1° (λ=436 nm, c=22 g/dm$^3$, CHCl$_3$)

Example 52

Hydrolysis of Cellulose Methylphenyl)Propionate (DS=3, Example 22)

Working as in Example 35, with 0.103 g of phase, 0.74 g of LiOH monohydrate, 60 ml of THF and hydrolysis for 72 h, 0.077 g (0.47 mmol) of p-methylphenylpropionic acid is obtained.

The hydrolysis yield is quantitative and the acid recovered is analyzed by NMR.

$^1$H NMR (CDCl$_3$, 200 MHz) δ (ppm): 1.4 (d, 3H, α-CH$_3$), 2.25 (s, 3H, CH$_3$—Ar), 3.6 (q, 1H, benzylic H), 7.03–7.16 (s, 4H, aromatic H), 9.5–10.5 (m, 1H, acid H).

The hydrolyzed phase recovered is analyzed by solid IR (KBr): its spectrum is identical to that of the starting cellulose.

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 98/1.95/0.05, 0.8 ml/min, %=230 nm. 2 peaks are obtained at Rt=12.02 min (62.4%) and Rt=13.53 min (37.6%).

The sign of the optical rotation indicates an enrichment in (−) enantiomer which thus corresponds to the 1st peak.

Optical Rotation:

$[\alpha]^{20}$=−15.6° (λ=589 nm, c=21 g/dm$^3$, CHCl$_3$).

$[\alpha]^{20}$=−18.6° (λ=436 nm, c=21 g/dm$^3$, CHCl$_3$).

Example 53

Hydrolysis of Cellulose
α-(2-Thiophenyl)Propionate (DS=1.98, Example 23)

Working as in Example 35, with 0.115 g of phase, 0.111 g of LiOH monohydrate, 50 ml of THF and hydrolysis for 72 h, 0.069 g (0.45 mmol) of 2-thiophenylpropionic acid is obtained.

The hydrolysis yield is quantitative and the acid recovered is analyzed by NMR.

$^1$H NMR (CDCl$_3$, 200 MHz) δ (ppm): 1.51 (d, 3H, α-CH$_3$), 3.95 (q, 1H, benzylic H), 6.9 (m, 2H, aromatic H), 7.15 (m, 1H, aromatic H), 9.5–9.8 (m, 1H, acid H).

The hydrolyzed phase recovered is analyzed by solid IR (KBr): its spectrum is identical to that of the starting cellulose.

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 99/0.95/0.05, 1 ml/min, λ=230 nm. 2 peaks are obtained at Rt=22.66 min (50.1%) and Rt=30.72 min (49.9%).

The optical rotation measurement confirms that the mixture is racemic.

Example 54

Hydrolysis of Cellulose
α-(2-Thiophenyl)Propionate (DS=2.85, Example 24)

Working as in Example 35, with 0.106 g of phase, 0.083 g of LiOH monohydrate, 50 ml of THF and hydrolysis for 72 h, 0.081 g (0.52 mmol) of 2-thiophenylpropionic acid is obtained.

The hydrolysis yield is quantitative and the acid recovered is analyzed by NMR.

$^1$H NMR (CDCl$_3$, 200 MHz) δ (ppm): 1.6 (d, 3H, α-CH$_3$), 4 (q, 1H, benzylic H), 6.95 (m, 2H, aromatic H), 7.2 (m, 1H, aromatic H), 10.7–11.3 (m, 1H, acid H).

The hydrolyzed phase recovered is analyzed by solid IR (KBr): its spectrum is identical to that of the starting cellulose.

The enantiomeric composition of this acid was determined by chiral HPLC on a Chiralcel OD-H column (250*4 mm, 5 μm, Daicel Japan) with the following analysis conditions: hexane/iPrOH/CF$_3$COOH: 99/0.95/0.05, 1 ml/min, λ=230 nm. 2 peaks are obtained at Rt=21.63 min (53.4%) and Rt=29.54 min (46.6%).

The sign of the optical rotation indicates an enrichment in (−) enantiomer which thus corresponds to the 1st peak.

Optical rotation: $[α]^{20}$ −1.7° (λ=589 nm, c=17 g/dm$^3$, CHCl$_3$).

Example 55

Hydrolysis of the Mixed Cellulose Phase Described in Example 25 (α-Phenylpropionic Acid DS=0.6+Ketoprofen DS=1.63)

Working as in Example 35, with 0.389 g of phase, 0.18 g of LiOH monohydrate, 60 ml of THF and hydrolysis for 48 h, 0.31 g of α-phenylpropionic acid and ketoprofen is obtained.

The hydrolysis yield for these two acids is quantitative.

The hydrolyzed phase recovered is analyzed by solid IR (KBr): its spectrum is identical to that of the starting cellulose.

The enantiomeric compositions of these two acids were determined by chiral HPLC on a Chiralcel OD-H column (250*4 mm, 5 μm, Daicel Japan) with the following analysis conditions: hexane/iPrOH/CF$_3$COOH: 98/1.95/0.05, 0.8 ml/min, λ=230 nm. 4 peaks are obtained: 2 peaks corresponding to λ-phenylpropionic acid at Rt=12.58 min (55%, R(−)) and Rt=14.75 min (45%, S(+)), and 2 peaks corresponding to ketoprofen at Rt=30.27 min (53.7%, R(−)) and Rt=32.56 min (46.3%, S(+)).

Example 56

Hydrolysis of Cellulose Naproxenate (Obtained from S(+) Naproxen, DS=2.7), Described in Example 27

110 mg (0.15 mmol) of ester to be hydrolyzed, 70 ml of THF, 10 ml of water and 63 mg (10 eq.) of lithium hydroxide monohydrate are placed in a 250 ml one-necked round-bottomed flask. The mixture is stirred at room temperature for 24 h. The THF is then evaporated off at room temperature and 10 ml of water are added to the evaporation residue. This mixture is treated with 2 ml of 2M NaOH and is then filtered through cotton wool to remove the unreacted cellulose. The aqueous solution obtained is extracted with CH$_2$Cl$_2$ in order to extract the organic impurities and the unreacted ester, and is then acidified to pH=1 with 3M HCl. The aqueous phase is extracted with diethyl ether. The ether phase is dried over MgSO$_4$ and the solvent is evaporated off. 70 mg of naproxen (yield=75%) are thus obtained. The enantiomeric composition of the acid recovered is determined by chiral HPLC on an (R—R)-Whelk-0-1 column (Lichrocart 250*4 mm, 5 μm, Merck) under the following analysis conditions: hexane/iPrOH/CH$_3$COOH: 80/19.5/0.5, d=1 ml/min, λ=230 nm. Two peaks are obtained at times Rt=6.98 min (57%) and Rt=11.43 min (43%).

The literature indicates that the 1st peak corresponds to the S(+) form.

Injection of the S(+) enantiomer alone under identical conditions confirms that it is the first of the two enantiomers to be eluted.

Example 56A

Hydrolysis of Cellulose Naproxenate (DS=0.49, Example 27A)

The process is performed as in Example 56. The hydrolysis yield is quantitative and the structure of the acid recovered is confirmed by NMR. The hydrolyzed phase recovered is analyzed by solid IR (KBr): its spectrum is identical to that of the starting cellulose.

The enantiomeric composition of this acid was determined by chiral HPLC under the same conditions as in Example 56. The percentages of the two enantiomers R(−) and S(+) are 48% and 52% respectively.

Example 57

Hydrolysis of Cellulose Naproxenate (Obtained from Racemic Naproxen, DS=2.6) Described in Example 28

Under the same conditions (see Example 56) as for the hydrolysis of the S(+) naproxen ester (DS=2.7, Example 26), 300 mg (0.38 mmol) of ester and 138 mg (8.6 eq.) of lithium hydroxide are reacted together. After work-up, 250 mg of naproxen (yield=98%) are obtained. The enantiomeric composition of the acid recovered is determined by chiral HPLC on an (R—R)-Whelk-0-1 column (Lichrocart 250*4 mm, 5 μm, Merck) under the following analysis conditions: hexane/EtOH/$CH_3COOH$: 80/19.5/0.5, d=1 ml/min, λ=230 nm. Two peaks are obtained at times Rt=5.66 min (56%) and Rt=8.29 min (44%) for the S(+) and R(−) enantiomers respectively.

Example 57A

Hydrolysis of Cellulose Naproxenate (DS=0.49, Example 28A)

The process is performed as in Example 56. The hydrolysis yield is quantitative and the structure of the acid recovered is confirmed by NMR. The hydrolyzed phase recovered is analyzed by solid IR (KBr): its spectrum is identical to that of the starting cellulose. The enantiomeric composition of this acid was determined by chiral HPLC under the same conditions as in Example 56. The percentages of the two enantiomers R(−) and S(+) are 44% and 56% respectively.

Example 58

Hydrolysis of Cellulose Naproxenate (Obtained from Racemic Naproxen, DS=1.7) Described in Example 29

The hydrolysis is carried out according to the usual method (Example 56) with 150 mg (0.29 mmol) of ester (DS=1.7) and 68 mg (5.6 eq.) of LiOH. After work-up, 110 mg of naproxen (yield=98%) are obtained. The enantiomeric composition of the acid recovered is determined by chiral HPLC on an (R—R)-Whelk-0-1 column (Lichrocart 250*4 mm, 5 μm, Merck) under the following analysis conditions: hexane/EtOH/$CH_3COOH$: 80/19.5/0.5, d=1 ml/min, λ=230 nm. Two peaks are obtained at times Rt=7.42 min (40%) and Rt=11.91 min (60%) for the S(+) and R(−) enantiomers respectively.

Example 58A

Hydrolysis of Cellulose Naproxenate (DS=3.00, Example 29A)

The process is performed as in Example 56. The hydrolysis yield is quantitative and the structure of the acid recovered is confirmed by NMR. The hydrolyzed phase recovered is analyzed by solid IR (KBr): its spectrum is identical to that of the starting cellulose. The enantiomeric composition of this acid was determined by chiral HPLC under the same conditions as in Example 56. The percentages of the two enantiomers R(−) and S(+) are 57% and 43% respectively.

Example 59

Hydrolysis of Cellulose Naproxenate (Obtained from Racemic Naproxen, DS=0.71) Described in Example 30

The hydrolysis is carried out according to the usual method (Example 56) with 150 mg (0.48 mmol) of ester (DS=0.71) and 54 mg (2.7 eq.) of LiOH. After work-up, 60 mg of naproxen (yield=76%) are obtained. The enantiomeric composition of the acid recovered is determined by chiral HPLC on an (R—R)-Whelk-0-1 column (Lichrocart 250*4 mm, 5 μm, Merck) under the following analysis conditions: hexane/EtOH/$CH_3COOH$: 80/19.5/0.5, d=1 ml/min, λ=230 nm. Two peaks are obtained at times Rt=7.34 min (45%) and Rt=11.74 min (55%) for the S(+) and R(−) enantiomers respectively.

Example 60

Hydrolysis of Cellulose Naproxenate (Obtained from S(+) Naproxen, DS=1.5) Described in Example 31

The hydrolysis is carried out according to the usual method (Example 56) with 293 mg (0.61 mmol) of ester (DS=1.5) and 170 mg (7 eq.) of LiOH. After work-up, 180 mg of naproxen (yield=86%) are obtained. The enantiomeric composition of the acid recovered is determined by chiral HPLC on an (R—R)-Whelk-0-1 column (Lichrocart 250*4 mm, 5 μm, Merck) under the following analysis conditions: hexane/EtOH/$CH_3COOH$: 80/19.5/0.5, d=1 ml/min, λ=230 nm. Two peaks are obtained at times Rt=8.44 min (47%) and Rt=14.18 min (53%) for the S(+) and R(−) enantiomers respectively.

Example 61

Hydrolysis of Cellulose Naproxenate (Obtained from S(+) Naproxen, DS=0.6) Described in Example 32

The hydrolysis is carried out according to the usual method (Example 56) with 330 mg (1.14 mmol) of ester (DS=0.6) and 48 mg (11.4 mmol, 10 eq.) of LiOH. After work-up, 150 mg of naproxen (yield=93%) are obtained. The enantiomeric composition of the acid recovered is determined by chiral HPLC on an (R—R)-Whelk-0-1 column (Lichrocart 250*4 mm, 5 μm, Merck) under the following analysis conditions: hexane/iPrOH/$CH_3COOH$: 80/19.5/0.5, d=1 ml/min, λ=230 nm. Two peaks are obtained at times Rt=6.94 min (47%) and Rt=10.46 min (53%) for the S(+) and R(−) enantiomers respectively.

Example 61A

Hydrolysis of Cellulose Naproxenate (DS=2.80, Example 32A)

The process is performed as in Example 56. The hydrolysis yield is quantitative and the structure of the acid recovered is confirmed by NMR. The hydrolyzed phase recovered is analyzed by solid IR (KBr): its spectrum is identical to that of the starting cellulose. The enantiomeric composition of this acid was determined by chiral HPLC under the same conditions as in Example 56. The percentages of the two enantiomers R(−) and S(+) are 55% and 45% respectively.

Example 62

Hydrolysis of α=Cyclodextrin Naproxenate: (DS=2.81, Example 34)

The process is performed as in Example 56. The hydrolysis yield is quantitative and the structure of the acid recovered is confirmed by NMR. The hydrolyzed phase recovered is analyzed by solid IR (KBr): its spectrum is identical to that of the starting β-cyclodextrin. The enantiomeric composition of this acid was determined by chiral HPLC under the same conditions as in Example 56. The percentages of the two enantiomers R(−) and S(+) are 50% and 50% respectively.

Example 63

Deracemization of Cellulose α-Phenylpropionate (DS=2.96, Example 1B) in Pyridine at 25° C.

50 mg of cellulose α-phenylpropionate of DS=2.96, obtained from the reaction described in Example 1B, and 2.7 ml of pyridine are placed in a pill bottle. The mixture is stirred at room temperature for 8 days. The solvent is evaporated off and hydrolysis is then carried out under the conditions described in Example 35. The hydrolysis yield is quantitative and the structure of the acid recovered is confirmed by NMR. The hydrolyzed phase recovered is analyzed by solid IR (KBr): its spectrum is identical to that of the starting cellulose. The enantiomeric composition of this acid was determined by chiral HPLC under the same conditions as in Example 35. The percentages of the two enantiomers R(−) and S(+) are 46% and 54% respectively.

Example 64

Deracemization of Cellulose β-Phenylpropionate (DS=2.96, Example 1B) in Pyridine at 90° C.

The process is performed as in Example 63, except that the mixture is stirred this time for 24 h at 90° C. The work-up and hydrolysis are carried out as in Example 63. The hydrolysis yield is quantitative and the structure of the acid recovered is confirmed by NMR. The hydrolyzed phase recovered is analyzed by solid IR (KBr): its spectrum is identical to that of the starting cellulose. The enantiomeric composition of this acid was determined by chiral HPLC under the same conditions as in Example 35. The percentages of the two enantiomers R(−) and S(+) are 49% and 51% respectively.

Example 65

Deracemization of Cellulose α-Phenylpropionate (DS=2.94, Example 1) in a Pyridine/Triethylamine/DMAP Mixture at 25° C.

50 mg of cellulose α-phenylpropionate of DS=2.94, obtained from the reaction described in Example 1, and 2.7 ml of a pyridine/triethylamine mixture in a 2/1 (v/v) proportion and a catalytic amount of DMAP are placed in a pill bottle. The mixture is stirred at room temperature for 8 days. The work-up and hydrolysis are carried out as in Example 63. The hydrolysis yield is quantitative and the structure of the acid recovered is confirmed by NMR. The hydrolyzed phase recovered is analyzed by solid IR (KBr): its spectrum is identical to that of the starting cellulose. The enantiomeric composition of this acid was determined by chiral HPLC under the same conditions as in Example 35. The percentages of the two enantiomers R(−) and S(+) are 61% and 39% respectively.

Example 66

Deracemization of Cellulose α-Phenylpropionate (DS=2.94, Example 1) in a Pyridine/Triethylamine/DMAP Mixture at 90° C.

The process is performed as in Example 65, except that the mixture is stirred this time for 24 h at 90° C. The work-up and hydrolysis are carried out as in Example 63. The hydrolysis yield is quantitative and the structure of the acid recovered is confirmed by NMR. The hydrolyzed phase recovered is analyzed by solid IR (KBr): its spectrum is identical to that of the starting cellulose. The enantiomeric composition of this acid was determined by chiral HPLC under the same conditions as in Example 35. The percentages of the two enantiomers R(−) and S(+) are 56% and 44% respectively.

Example 67

Deracemization of Cellulose α-Phenylpropionate (DS=2.94, Example 1) in a Pyridine/DABCO/DMAP Mixture at 90° C.

The process is performed as in Example 66, except that the mixture consists this time of 1 ml of pyridine, 0.5 g of DABCO (1,4-diazabicyclo[2.2.2]octane) and a catalytic amount of DMAP. After reaction, the mixture is poured into 10 ml of methanol. The cellulose ester thus precipitated is filtered off and dried. The hydrolysis of this ester is carried out as in Example 63. The hydrolysis yield is quantitative and the structure of the acid recovered is confirmed by NMR. The hydrolyzed phase recovered is analyzed by solid IR (KBr): its spectrum is identical to that of the starting cellulose. The enantiomeric composition of this acid was determined by chiral HPLC under the same conditions as in Example 35. The percentages of the two enantiomers R(−) and S(+) are 46% and 54% respectively.

D—Chromatographic Evaluation of the Esters Synthesized and Used as Chiral Stationary Phases Procedure and Principle:

4 mg of stationary phase to be tested and 100 µl of a solution of the test racemic mixture, with a concentration of between 0.5 and 1 mg/ml (depending on the solubility of the compound), are introduced into a pill bottle and then maintained at 10° C. for 2 h in order to allow the test compound to be adsorbed onto the stationary phase. 25 µl of supernatant are taken under cold conditions, by decantation or filtration, and are diluted (concentration specific to each racemic mixture) using the analysis eluent adapted to the racemate under consideration. The same dilution operation is carried out using 25 µl of the initial solution of the racemic mixture. The solutions are injected on chiral HPLC under analysis conditions specific to each racemate. Chromatographic analysis of the supernatant makes it possible, by comparison with the racemic mixture, to determine the enrichment (E), the adsorption of the compound on the chiral phase (ads) and the enantioselectivity (a) of the phase with respect to the compound under consideration.

Description of the Tables:

TABLE 1: Chromatographic evaluation of cellulose esters and amylose esters by the "microbatch" method in a 99/1 hexane/2-propanol eluent. Benzoin, Tröger's base and Pirkle's alcohol were injected onto a Chiralpak AS column in 90/10 hexane/2-propanol, trans-stilbene oxide was injected onto the Chiralcel OD-H column in 90/10 hexane/2-propanol.

The definitions of the terms used in this table are as follows:

⇒ads: adsorption=$(1-[(Atrac \times A^{1.2}) \div (Arac^{1.2} \times At)]) \times 100$
⇒E: enrichment=difference in the concentrations of the two enantiomers of the test compound after adsorption on the phase.
⇒a: enantioselectivity=$([(Arac^2 \times At)/(Atrac \times A^2)]-1) \div ([(Arac^1 \times At) \div (Atrac \times A^1)]-1)$ Atrac: area of the 1,3,5-tris t-butylbenzene (TTB) in the racemic mixture. The TTB serves to measure the dead volume of the column.

$Arac^1$: area, in the racemic mixture, of the peak corresponding to the enantiomer which is least adsorbed onto the test phase.

$Arac^2$: area, in the racemic mixture, of the peak corresponding to the enantiomer which is most adsorbed onto the test phase.

At: area of the 1,3,5-tris t-butylbenzene (TTB) in the supernatant solution.

$A^1$: area of the enantiomer which is least adsorbed onto the test phase.

$A^2$: area of the enantiomer which is most adsorbed onto the test phase.

TABLE 2: Order of elution, configuration and enantioselectivity of the 4 test compounds on the commercial phases from Daicel: cellulose tris(4-methylbenzoate) (Chiralcel OJ), cellulose tris(3,5-dimethylphenylcarbamate) (Chiralcel OD), amylose tris[(S)-α-phenethylcarbamate] (Chiralpak AS) in a 90/10 hexane/2-propanol eluent.

The definitions of the terms used in this table are as follows:

a: enantioselectivity=(retention factor of the enantiomer which is most adsorbed)÷(retention factor of the enantiomer which is least adsorbed).

Comments and Results:

The cellulose esters and polysaccharide esters of the present invention show strong adsorption for benzoin and Pirkle's alcohol and moderate adsorption for Trögers base and trans-stilbene oxide.

The comparison between the test phases and the commercial phases (Table 2) reveals, for certain racemates, comparable enantioselectivities (α) between the two series of phases with appreciable adsorptions and inversions of order of elution. By way of nonlimiting example, the comparison of the adsorption of these racemates on the test phases and on the commercial phases Chiracel OJ, Chiralcel OD and Chiralpak AS shows inversions of order of elution: specifically, the benzoin enantiomer predominantly adsorbed onto the test stationary phases has the S(+) configuration as in the case of Chiralcel OJ, but the order is inverted for Chiralcel OD and Chiralpak AS. In the case of Pirkle's alcohol, an inversion of the order of elution is observed between the test phases and the three commercial phases. In the case of trans-stilbene oxide, although the adsorptions are weaker than in the previous two cases, an identical order for Chiralcel OD is noted, but an inverse order is noted relative to the other two commercial phases. These inversions of order of elution are very useful when it is desirable to have one enantiomer, in particular, which is eluted first.

Some of these phases also show enantioselectivities that are comparable to the commercial phases with appreciable adsorptions, for instance cellulose α-phenylpropionate DS=2.5 (Example 3, Table 1) which shows an a =1.3 for benzoin, which is identical to that of Chiralcel OJ under the same analysis conditions. Mention may also be made of the cellulose 3,5-dimethylphenylpropionate DS=3 phase (Example 21, Table 1) or the cellulose p-methylphenylpropionate DS=3 phase (Example 22, Table 1), which show a values of 1.25 and 1.27, respectively, for trans-stilbene oxide (α=1.17 for Chiralcel OJ and α=1.28 for Chiralpak AS), cellulose p-methylphenylpropionate DS=3 phase (Example 22, Table 1) also gives good resolution for Tröger's base with an α value of 1.3 (α=1.32 for Chiralcel OD). By way of nonlimiting example, the latter phase thus has an enantioselectivity which respect to trans-stilbene oxide which is better than that of Chiralcel OJ, with an inversion of the order of elution relative to this commercial phase.

TABLE 1

| TEST ESTER | BENZOIN | | | | TRÖGER'S BASE | | | | TRANS-STILBENE OXIDE | | | | PIRKLE'S ALCOHOL | | | |
|---|---|---|---|---|---|---|---|---|---|---|---|---|---|---|---|---|
| | Ads 1 | Ads 2 | E | α | Ads 1 | Ads 2 | E | α | Ads 1 | Ads 2 | E | α | Ads 1 | Ads 2 | E | α |
| Cellulose α-phenylpropionate DS = 2.5 (pyridine) Example 3 | 54 | 48 | 6 | 1.3 | 17 | 17.6 | 0.3 | 1.07 | 18 | 20 | 1 | 1.11 | 63 | 62 | 1 | 1.03 |
| Cellulose α-phenylpropionate DS = 2.5 (toluene/pyridine) Example 4 | 54 | 50 | 4 | 1.18 | 29 | 29 | 0 | 1 | 31 | 29 | 2 | 1.13 | 61 | 60 | 0.5 | 1.01 |
| Amylose α-phenylpropionate DS = 3 (pyridine) Example 8 | 37 | 36 | 1 | 1.05 | 17.2 | 15.8 | 1 | 1.1 | 17 | 19 | 1 | 1.1 | 49 | 50 | 0.5 | 1.03 |
| Cellulose p chlorophenyl-propionate DS = 3 Example 10 | 94.5 | 93.7 | 7.2 | 1.17 | 70 | 70 | 0.5 | 1 | 12 | 13 | 0.5 | 1.09 | 60 | 60 | 0.9 | 1 |

TABLE 1-continued

| TEST ESTER | BENZOIN | | | | TRÖGER'S BASE | | | | TRANS-STILBENE OXIDE | | | | PIRKLE'S ALCOHOL | | | |
|---|---|---|---|---|---|---|---|---|---|---|---|---|---|---|---|---|
| | Ads 1 | Ads 2 | E | α | Ads 1 | Ads 2 | E | α | Ads 1 | Ads 2 | E | α | Ads 1 | Ads 2 | E | α |
| Amylose p-chlorophenyl-propionate DS = 3 Example 13 | 81.8 | 81.3 | 1.4 | 1.03 | 80 | 80 | 1.2 | 1 | 12 | 12 | 0 | 1 | 70 | 69 | 2.1 | 1.03 |
| Cellulose ketoprofenate DS = 2.35 (pyridine) Example 14 | 46 | 46.6 | 0.7 | 1.03 | 2.5 | 3.1 | 0.2 | 1.25 | 4 | 5.5 | 0.7 | 1.4 | 15.7 | 16.3 | 0.1 | 1.05 |
| Cellulose ketoprofenate DS = 2.9 (pyridine /Et$_3$N/DMAP) Example 15 | 39 | 37 | 1.7 | 1.08 | 18 | 18 | 0.1 | 1 | 20 | 20 | 0.5 | 1 | 28 | 28 | 0.4 | 1 |
| Amylose ketoprofenate DS = 2.42 Example 16 | 74 | 74 | 0 | 1 | 50 | 50 | 0.1 | 1 | 0.3 | 0.3 | 0.3 | 1 | 52 | 52 | 1 | 1 |
| Cellulose α-(3,5-dimethylphenyl)-propionate DS = 3 Example 21 | 65.4 | 63.2 | 2.95 | 1.1 | 14.8 | 14.4 | 0.8 | 1.04 | 11.5 | 13.9 | 1.4 | 1.25 | 65.4 | 64.5 | 1.5 | 1.04 |
| Cellulose α-(p-methylphenyl)-propionate DS = 3 Example 22 | 64.6 | 61.7 | 3.8 | 1.13 | 11.6 | 14.4 | 1 | 1.3 | 16.1 | 19.5 | 1.73 | 1.27 | 71.6 | 71 | 1.5 | 1.04 |
| Cellulose α-(2-thiophenyl)-propionate DS = 2.85 Example 24 | 71.8 | 70 | 2.3 | 1.08 | 15.1 | 16 | 0.04 | 1.07 | 19.9 | 20.3 | 0.11 | 1.03 | 62.5 | 62 | 0.9 | 1.02 |
| Mixed cellulose ester: α-phenyl-propionic acid + ketoprofen DS = 0.6 + 1.63 Example 25 | 1 | 0 | 0.4 | | 11 | 11 | 1.1 | 1 | 0 | 0 | | | 0 | 0 | | |
| Mixed cellulose ester: ketoprofen + α-phenyl-propionic acid DS = 1 + 0.55 Example 26 | 57.8 | 55.3 | 2.6 | 1.1 | 17 | 17 | 0.5 | 1 | 18 | 18 | 0.6 | 1 | 43 | 43 | 0 | 1 |
| Cellulose naproxenate (S(+)) DS = 2.8 (pyridine/ Et$_3$N/DMAP) Example 27 | 88.5 | 88.7 | 0.4 | 1 | 9.8 | 10.1 | 0.5 | 1.04 | 2 | 1.4 | 0.2 | 1.47 | 1.3 | 1.1 | 0.2 | 1.3 |
| Cellulose naproxenate (RS) DS = 2.6 (pyridine/ Et$_3$N/DMAP) Example 28 | 88.5 | 88.7 | 0.4 | 1 | 9.8 | 10.1 | 0.5 | 1.04 | 2 | 1.4 | 0.2 | 1.47 | 1.3 | 1.1 | 0.2 | 1.3 |
| Amylose naproxenate (S(+)) DS = 2.3 (pyridine/ Et$_3$N/DMAP) Example 33 | 62 | 61 | 1.2 | 1.04 | 33 | 33 | 0.5 | 1 | 29 | 29 | 0.3 | 1 | 78 | 78 | 0.7 | 1 |

TABLE 2

| TEST ESTER | BENZOIN | | | TRÖGER'S BASE | | | TRANS-STILBENE OXIDE | | | PIRKLE'S ALCOHOL | | |
|---|---|---|---|---|---|---|---|---|---|---|---|---|
| | 1st eluted | 2nd eluted | α | 1st eluted | 2nd eluted | α | 1st eluted | 2nd eluted | α | 1st eluted | 2nd eluted | α |
| Chiralcel OD 90/10 hexane/ 2-propanol | S(+) | R(−) | 1.58 | (+) | (−) | 1.32 | SS(−) | RR(+) | 1.68 | (−) | (+) | 2.59 |
| Chiralcel OJ 90/10 hexane/ 2-propanol | R(−) | S(+) | 1.23 | (+) | (−) | 3.8 | RR(+) | SS(−) | 1.17 | (−) | (+) | 1.14 |
| Chiralpak AS 90/10 hexane/ 2-propanol | S(+) | R(−) | 1.9 | (+) | (−) | 2.38 | RR(+) | SS(−) | 1.28 | (−) | (+) | 1.88 |

We claim:

1. An ester of a polysaccharide which is chiral in the acyl moiety of the ester and which is obtained by reacting, in a basic solvent, at least one polysaccharide and at least one acid or acid derivative of formula (I):

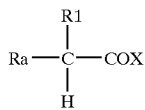

(I)

in which
X corresponds to a hydroxyl or to a halogen, Ra represents an aryl, aralkyl, aralkenyl, alkylaryl or alkenylaryl radical, a 6-methoxy-2-naphthalenyl, chlorophenyl, dimethylphenyl or thiophenyl group and
$R^1$ represents a linear $C_1$–$C_{20}$-alkyl-radical, a branched $C_1$–$C_{20}$ alkyl-radical or a cyclic $C_3$–$C_{20}$-alkyl-radical, with the proviso that when $R^1$ is —$CH_3$ then Ra is not a phenyl, the acyl units attached to said polysaccharide being not all of identical chirality.

2. The ester according to claim 1, wherein said acyl units attached to said polysaccharide are of both R and S configuration with a majority of R configuration versus S configuration.

3. The ester according to claim 1, wherein said acyl units attached to said polysaccharide are of both R and S configuration with a majority of S configuration versus R configuration.

4. The ester according to claim 2, wherein the proportion of said acyl units of R configuration is between 50% and 70%.

5. The ester according to claim 3, wherein the proportion of said acyl units of S configuration is between 50% and 60%.

6. The ester according to claim 1, wherein the degree of substitution (DS) of each monomer unit of said polysaccharide is between 0.5 and 3.

7. The ester according to claim 1, wherein in formula (I) of the acid or acid derivative:
Ra corresponds to a substituent comprising at least one phenyl or at least one naphthyl and
$R^1$ corresponds to a methyl, an ethyl or a propyl.

8. The ester according to claim 1 wherein, in formula (I), X corresponds to Cl.

9. The ester according to claim 1, wherein the polysaccharides of which they are constituted are selected from the group consisting of cellulose and starch.

10. Mixed ester of a polysaccharide which is chiral in the acyl moiety of the ester and which is obtained by reacting at least one polysaccharide with:
at least one acid or acid derivative of formula (I):

(I)

in which
X corresponds to a hydroxyl or to a halogen, Ra represents an aryl, aralkyl, aralkenyl, alkylaryl or alkenylaryl radical, a 6-methoxy-2-naphthalenyl, chlorophenyl, dimethylphenyl or thiophenyl group and
$R^1$ represents a linear $C_1$–$C_{20}$-alkyl-radical, a branched $C_1$–$C_{20}$ alkyl-radical or a cyclic $C_3$–$C_{20}$-alkyl-radical,
in a basic solvent,
and at least one other acid or acid derivative (I') which is different from the acid or from the acid derivative(s) (I), this other reagent (I') being chosen from the chiral compounds of formula (I) or from chiral or achiral compounds selected from the group comprising acetic acid, propionic acid, benzoic acid and carbamic acid, the acyl units attached to said polysaccharide being not all of identical chirality.

11. The ester according to claim 1 which is selected from the group consisting of the following esters comprising acyl units of both R and S configuration with a majority of R configuration:
amylose α-chlorophenylpropionate
cellulose α-chlorophenylpropionate
cellulose α-(3,5-dimethylphenyl)propionate
cellulose α-(para-methylphenyl)propionate
cellulose α-(2-thiophenyl)propionate
a mixed cellulose ester of α-phenylpropionic acid and of ketoprofen
cellulose ibuprofenate
cellulose naproxenate
amylose naproxenate and
beta-cyclodextrin naproxenate.

12. The ester according to claim 1 which is selected from the group consisting of the following esters comprising acyl units of both R and S configuration with a majority of S configuration:
amylose α-chlorophenylpropionate
cellulose α-chlorophenylpropionate
cellulose α-(3,5-dimethylphenyl)propionate
cellulose α-(para-methylphenyl)propionate cellulose α-(2-thiophenyl)propionate
a mixed cellulose ester of α-phenylpropionic acid and of ketoprofen
cellulose ketoprofenate
amylose ketoprofenate
cellulose ibuprofenate
cellulose naproxenate
amylose naproxenate and
beta-cyclodextrin naproxenate.

13. A process for preparing an ester according to any one of claims 1 to 12, consisting essentially in reacting cellulose with at least one acid chloride of formula (I), in a base selected from the group consisting of pyridine alone, a pyridine/4-(N,N-dimethylamino)-pyridine (DMAP) mixture, or 4-picoline alone, whereby giving cellulose esters comprising said acyl units of both R and S configuration with a majority of R configuration, the esters formed being recovered by carrying out at least one precipitation/dissolution sequence.

14. A process for preparing the esters according to any one of claims 1 to 12 consisting essentially in reacting cellulose with at least one acid chloride of formula (I), in a solvent selected from the group consisting of a pyridine/triethylamine/DMAP mixture and 2-picoline alone, whereby giving cellulose esters comprising said acyl units of both R and S configuration with a majority of S configuration, the esters formed being recovered by carrying out at least one precipitation/dissolution sequence.

15. A process for the chiral enrichment of racemates, comprising the steps which consist essentially:
1. in using acids or acid derivatives in racemic or enantiomerically pure form, as starting materials to prepare the esters according to claim 1, and
2. in hydrolyzing the esters thus formed, preferably using a base.

16. The process according to claim 15, wherein the hydrolysis in step -2- which is carried out is a total or partial hydrolysis of the ester functions, so as to predominantly release one of the two enantiomers of the starting acid or acid derivative (II).

17. The process according to claim 15 wherein before the hydrolysis in step -2-, a step -1a- of deracemization of above said chiral esters is carried out.

18. Enantioselective chiral chromatography support, comprising an ester according to claim 1.

19. Medicinal product, which is an ester of a polysaccharide according to claim 1, which comprises at least one active principle and which is capable, by hydrolysis, of releasing the active principle(s) in a sustained and controlled manner, the acid precursor(s) of formula (I) constituting the active principle(s).

20. The ester according to claim 11 comprising between 50% and 70% of units of R configuration.

21. The ester according to claim 12 comprising between 50% and 60% of units of S configuration.

22. The ester according to claim 9, wherein the polysaccharides are selected from the group consisting of amylose and amylopectin.

23. The process for the chiral enrichment of racemates according to claim 15, wherein step 2 is carried out using a hydroxylated base.

24. The process for the chiral enrichment of racemates according to claim 23, wherein the hydroxylated base is lithium hydroxide.

25. The process according to claim 17, wherein step 1a is carried out using one or more nitrogen bases selected from the group consisting of triethylamine, pyridine, picoline, 4-(N,N-dimethylamino)-pyridine (DMAP), 1,4-diazabicyclo[2.2.2]-octane (DABCO) and quinoline.

26. Enantioselective chiral chromatography support, comprising an ester obtained by the process according to claim 13.

27. Enantioselective chiral chromatography support, comprising an ester obtained by the process according to claim 14.

* * * * *